(12) United States Patent
Vogt

(10) Patent No.: US 7,297,480 B2
(45) Date of Patent: Nov. 20, 2007

(54) METHOD FOR DETECTION OF MELANOMA

(75) Inventor: Thomas Vogt, Pentling-Grossberg (DE)

(73) Assignee: Dermtech International, San Diego, CA (US)

( * ) Notice: Subject to any disclaimer, the term of this patent is extended or adjusted under 35 U.S.C. 154(b) by 475 days.

(21) Appl. No.: 10/184,846

(22) Filed: Jun. 27, 2002

(65) Prior Publication Data

US 2003/0108896 A1    Jun. 12, 2003

Related U.S. Application Data

(60) Provisional application No. 60/302,348, filed on Jun. 28, 2001.

(51) Int. Cl.
*C12Q 1/68* (2006.01)
*C12P 19/34* (2006.01)

(52) U.S. Cl. .............. 435/6; 435/912; 436/63; 436/64

(58) Field of Classification Search ............ 435/6, 435/91.2; 536/23.5, 24.31, 24.33
See application file for complete search history.

(56) References Cited

U.S. PATENT DOCUMENTS

| | | |
|---|---|---|
| 4,537,776 A | 8/1985 | Cooper |
| 4,971,800 A | 11/1990 | Chess et al. |
| 5,460,939 A | 10/1995 | Hansbrough et al. |
| 5,753,612 A | 5/1998 | Mitrani |
| 5,811,239 A | 9/1998 | Frayne |
| 6,054,277 A | 4/2000 | Furcht et al. |
| 6,056,859 A | 5/2000 | Ramsey et al. |
| 6,355,439 B1 | 3/2002 | Chung et al. |

OTHER PUBLICATIONS

Benson et al. 2006. Journal of Investigative Dermatology. 126: 2234-2241.*
S.A. J. Ijland et al. "Expression of Angiogenic and Immunosuppressive Factors by Uveal Melanoma Cell Lines," *Melanoma Research*, vol. 9, 1999, pp. 445-450.
Database EMBASE on STN, AN 96134300, McKenzie et al. "Interleukin-1 receptor antagonist inhibits subcutaneous B16 melanoma growth in vivo," Anticancer Research, 1996, vol. 16, No. 1, pp. 437-441, see abstract.
Database CAPLUS on STN, Graengsjoe et al., "Early differences in the epidermal elemental content and expression of cytokines after application of 2 different irritants," Contact Dermatitis, 1996, vol. 35, No. 6, pp. 355-360, see abstract.
Bittner et al., "Molecular classification of cutaneous malignant melanoma by gene expression profiling", *Nature*, 406:536-540 (2000).
Cosini and Galli, "Cytokines and Irritant Contact Dermatitis," *Toxicology Letters*, 102-103:277-282, Elsevier (1998).

Davy and Robbins, "Ephrin-A5 modulates cell adhesion and morphology in an integrin-dependent manner", *EMBO J.*, 19(20):5396-5403 (2000).
Dekker et al., "Characterization of interleukin-1 alpha-induced melanoma cell motility: inhibition by type I and type II receptor-blocking monoclonal antibodies", *Melanoma Res.*, 7(3):223-230 (1997).
Dreher et al., "Colorimetric Method for Quantifying Human *Stratum corneum* Removed by Adhesive-Tape Stripping," *Acta Derma Venereol*, 78:186-189, Scandinavian University Press (1998).
Easty et al., "Up-regulation of ephrin-A1 during melanoma progression", *Int. J. Cancer*, 84:494 (1999).
Farage, M.A. et al., "Further Development of Noninvasive Method for Assessing Human Skin Irritation," Abstract # 1909, The Proctor & Gamble Company, (1998).
Freedberg et al., "Keratins and the Keratinocyte Activation Cycle," *The Journal of Investigative Dermatology*, 116(5):633-640, The Society for Investigative Dermatology, Inc. (2001).
Garofano, L. et al., "PCR based analysis of epidermal cells found on adhesive tape," *Advances in Forensic Haemogenetic*, vol. 6:281-283 (1996). (*Istituto di Anatomia e Fisiologia Umana, Universita degli Studi ti Torino, Italy*).
Garofano, L. et al.,"Comparison of Powerplex® 16 System and Other Multiplex STR Typing Kits on Casework," (*Reporto Carabinieri Investigazioni Scientifiche, Parma, Italia.*), 2000. Reference available at: <Url:promega.com/geneticidproc/ussymp11proc/content/garofano.pdf>.
Goldschmidt and Kligman, "Desquamation of the Human Horny Layer," *Arch. Derm*, 95:583-586, American Medical Association (1967).
Hamid et al., "In Vivo Expression of IL-12 and IL-13 in Atopic Dermatitis," *Journal of Allergy and Clinical Immunology*, 98(1):1-8, Mosby-Year Book, Inc. (1996).
Hirao et al., "Elevation of Interleukin 1 Receptor Antagonist in the Stratum Corneum of Sun-Exposed and Ultraviolet B-Irradiated Human Skin," *The Journal of Investigative Dermatology*, 106(5):1102-1107, The Society for Investigative Dermatology, Inc. (1996).
Hojyo-Tomoka and Kligman, "Does Cellophane Tape Stripping Remove the Horny Layer?" *Arch. Derm.*, 106(5):767-768 (1972).
Junghans et al., "Epidermal Cytokines IL-1β, TNF-α, and IL-12 in Patients with Atopic Dermatitis: Response to Application of House Dust Mite Antigens," *The Journal of Investigative Dermatology*, 111(6):1184-1188, The Society for Investigative Dermatology, Inc. (1998).

(Continued)

*Primary Examiner*—Carla J. Myers
(74) *Attorney, Agent, or Firm*—DLA Piper US LLP

(57) ABSTRACT

The present invention provides non-invasive methods for detecting, monitoring, staging, and diagnosing malignant melanoma in a skin sample of a subject. The methods include analyzing expression in skin sample of one or more melanoma skin markers. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. The skin sample can include nucleic acids, and can be a human skin sample from a lesion suspected of being melanoma.

18 Claims, 5 Drawing Sheets

OTHER PUBLICATIONS

Katz et al., "Skin-Surface Touch Print for Diagnosing Fungal Infections," *American Family Physician*, 31(4):189-194, American Academy of Family Physicians (1985).

Klaschka and Norenberg, "Individual Transparency Patterns of Adhesive-Tape Strip Series of the Stratum Corneum," *International Journal of Dermatology*, 16(10):836-841, J.B. Lippincott Company (1997).

Klaschka and Nörenberg, "New Measuring Device of Horny Layer Transparency," *Arch. Derm. Res.*, 254:313-325, Springer-Verlag (1975).

Kondo et al., "Characterization of Epidermal Cytokine Profiles in Sensitization and Elicitation Phases of Allergic Contact Dermatitis as Well as Irritant Contact Dermatitis in Mouse Skin," *Lymphokine and Cytokine Research*, 13(6):367-375, Mary Ann Liebert, Inc. (1994).

Marttin et al., "A Critical Comparison of Methods to Quantify Stratum corneum Removed by Tape Stripping," *Skin Pharmacol.*, 9:69-77 S. Karger AG (1996).

Nickoloff and Naidu, "Perturbation of Epidermal Barrier Function Correlates with Initiation of Cytokine Cascade in Human Skin," *Journal of the American Academy of Dermatology*, 30(4):535-546, American Academy of Dermatology, Inc. (1994).

Nickoloff et al., "Keratinocyte Interleukin-10 Expression is Upregulated in Tape-Stripped Skin, Poison Ivy Dermatitis, and Sezary Syndrome, but Not in Psoriatic Plaques," *Clinical Immunology and Immunopathology*, 73(1):63-68, Academic Press, Inc. (1994).

Ohmen et al., "Overexpression of IL-10 in Atopic Dermatitis," *The Journal of Immunology*, 154:1956-1963, The American Association of Immunologists (1995).

Onodera S., et al. "Macrophage Migration Inhibitory Factor Up-regulates Expression of Matrix Metalloproteinases in Synovial Fibroblasts of Rheumatoid Arthritis", *J. Biol. Chem*, 275:444-450 (2000).

Paludan, K. and Thestrup-Pedersen, K., "Use of the Polymerase Chain Reaction in Quantification of Interleukin 8 mRNA in Minute Epidermal Samples", *The Journal of Investigative Dermatology*, vol. 99, No. 6, Dec. 1992.

Perkins et al., "Development of a Noninvasive Method for Assessing Human Skin Irritation," *The Toxicologist*, 36(1):365, Academic Press, Inc. (1997).

Perkins et al., "A Noninvasive Method to Assess Skin Irritation and Compromised Skin Conditions Using Simple Tape Adsorption of Molecular Markers of Inflammation," *Skin Res. Technol.*, 7(4):227-237 (2001).

Potts and Francoeur, "Physical Methods for Studying Stratum Corneum Lipids," *Seminars in Dermatology*, 11(2):129-138, W.B. Saunders Company (1992).

Ryan and Gerberick, "Cytokine mRNA Expression in Human Epidermis after Patch Treatment with Rhus and Sodium Lauryl Sulfate," *American Journal of Contact Dermatitis*, 10(3):127-135, W.B. Saunders Company (1999).

Torre and Gino, "Epidermal Cells on Stubs Used for Detection of GSR with SEM-EDX: Analysis of DNA Polymorphisms," *Journal of Forensic Sciences*, JFSCA, vol. 41, No. 4, Jul. 1996, pp. 658-659.

van der Molen et al., Tape Stripping of Human Stratum Corneum Yields Cell Layers that Originate from Various Depths because of Furrows in the Skin, *Arch. Dermatol. Res.*, 289:514-518, Springer-Verlag (1997).

van der Valk and Maibach, "A Functional Study of the Skin Barrier to Evaporative Water Loss by Means of Repeated Cellophane-Tape Stripping," *Clinical and Experimental Dermatology*, 15(3):180-182 (1990).

van Hoogdalem, "Assay of Erythromycin in Tape Strips of Human Stratum corneum and Some Preliminary Results in Man," *Skin Pharmacol.*, 5:124-128, S. Karger AG (1992).

Weigand and Gaylor, "Removal of Stratum Corneum in Vivo: An Improvement on the Cellophane Tape Stripping Technique," *The Journal of Investigative Dermatology*, 60(2)84-87, The Williams & Wilkins Co. (1973).

Yawalkar and Pichler, "Pathogenesis of Drug-Induced Exanthema," *Int. Arch. Allergy Immunol.*, 124:336-338, S. Karger AG (2001).

* cited by examiner

SEQUENCE LISTING

<160> NUMBER OF SEQ ID NOS: 28

<210> SEQ ID NO 1
<211> LENGTH: 20
<212> TYPE: DNA
<213> ORGANISM: Artificial sequence
<220> FEATURE:
<223> OTHER INFORMATION: PCR primer

<400> SEQUENCE: 1
ttcaggacat tactattgcg                                               20

<210> SEQ ID NO 2
<211> LENGTH: 20
<212> TYPE: DNA
<213> ORGANISM: Artificial sequence
<220> FEATURE:
<223> OTHER INFORMATION: Target sequence

<400> SEQUENCE: 2
cgcaatagta atgtcctgaa                                               20

<210> SEQ ID NO 3
<211> LENGTH: 21
<212> TYPE: DNA
<213> ORGANISM: Artificial sequence
<220> FEATURE:
<223> OTHER INFORMATION: PCR primer

<400> SEQUENCE: 3
ttccacactg taatagtctt c                                             21

<210> SEQ ID NO 4
<211> LENGTH: 21
<212> TYPE: DNA
<213> ORGANISM: Artificial sequence
<220> FEATURE:
<223> OTHER INFORMATION: Target sequence

<400> SEQUENCE: 4
gaagactatt acagtgtgga a                                             21

<210> SEQ ID NO 5
<211> LENGTH: 17
<212> TYPE: DNA
<213> ORGANISM: Artificial sequence
<220> FEATURE:
<223> OTHER INFORMATION: PCR primer

<400> SEQUENCE: 5
ctgccaaggc gctgtca                                                  17

<210> SEQ ID NO 6
<211> LENGTH: 17
<212> TYPE: DNA
<213> ORGANISM: Artificial sequence
<220> FEATURE:
<223> OTHER INFORMATION: Target sequence

<400> SEQUENCE: 6
tgacagcgcc ttggcag                                                  17

<210> SEQ ID NO 7
<211> LENGTH: 18

```
<212> TYPE: DNA
<213> ORGANISM: Artificial sequence
<220> FEATURE:
<223> OTHER INFORMATION: PCR primer

<400> SEQUENCE: 7
tcagtccagg gccttcga                                                        18

<210> SEQ ID NO 8
<211> LENGTH: 18
<212> TYPE: DNA
<213> ORGANISM: Artificial sequence
<220> FEATURE:
<223> OTHER INFORMATION: Target sequence

<400> SEQUENCE: 8
tcgaaggccc tggactga                                                        18

<210> SEQ ID NO 9
<211> LENGTH: 13
<212> TYPE: DNA
<213> ORGANISM: Artificial sequence
<220> FEATURE:
<223> OTHER INFORMATION: Probe sequence

<400> SEQUENCE: 9
tgccagggac ccc                                                             13

<210> SEQ ID NO 10
<211> LENGTH: 13
<212> TYPE: DNA
<213> ORGANISM: Artificial sequence
<220> FEATURE:
<223> OTHER INFORMATION: Target sequence

<400> SEQUENCE: 10
ggggtccctg gca                                                             13

<210> SEQ ID NO 11
<211> LENGTH: 24
<212> TYPE: DNA
<213> ORGANISM: Artificial sequence
<220> FEATURE:
<223> OTHER INFORMATION: PCR primer

<400> SEQUENCE: 11
aacatgctgc acttgaagaa gaga                                                 24

<210> SEQ ID NO 12
<211> LENGTH: 24
<212> TYPE: DNA
<213> ORGANISM: Artificial sequence
<220> FEATURE:
<223> OTHER INFORMATION: Target sequence

<400> SEQUENCE: 12
tctcttcttc aagtgcagca tgtt                                                 24

<210> SEQ ID NO 13
<211> LENGTH: 21
<212> TYPE: DNA
<213> ORGANISM: Artificial sequence
<220> FEATURE:
<223> OTHER INFORMATION: PCR sequence

<400> SEQUENCE: 13
```
gaagctttct gatcgcgttc a                                      21

<210> SEQ ID NO 14
<211> LENGTH: 21
<212> TYPE: DNA
<213> ORGANISM: Artificial sequence
<220> FEATURE:
<223> OTHER INFORMATION: Target sequence

<400> SEQUENCE: 14
tgaacgcgat cagaaagctt c                                      21

<210> SEQ ID NO 15
<211> LENGTH: 15
<212> TYPE: DNA
<213> ORGANISM: Artificial sequence
<220> FEATURE:
<223> OTHER INFORMATION: Probe sequence

<400> SEQUENCE: 15
ccggctgggt gacat                                             15

<210> SEQ ID NO 16
<211> LENGTH: 15
<212> TYPE: DNA
<213> ORGANISM: Artificial sequence
<220> FEATURE:
<223> OTHER INFORMATION: Target sequence

<400> SEQUENCE: 16
atgtcaccca gccgg                                             15

<210> SEQ ID NO 17
<211> LENGTH: 18
<212> TYPE: DNA
<213> ORGANISM: Artificial sequence
<220> FEATURE:
<223> OTHER INFORMATION: PCR primer

<400> SEQUENCE: 17
gcgtgtgcgt gtgcaaga                                          18

<210> SEQ ID NO 18
<211> LENGTH: 18
<212> TYPE: DNA
<213> ORGANISM: Artificial sequence
<220> FEATURE:
<223> OTHER INFORMATION: Target sequence

<400> SEQUENCE: 18
tcttgcacac gcacacgc                                          18

<210> SEQ ID NO 19
<211> LENGTH: 17
<212> TYPE: DNA
<213> ORGANISM: Artificial sequence
<220> FEATURE:
<223> OTHER INFORMATION: PCR primer

<400> SEQUENCE: 19
cagccgctcg ggtaggt                                           17

<210> SEQ ID NO 20
<211> LENGTH: 17
<212> TYPE: DNA
<213> ORGANISM: Artificial sequence

```
<220> FEATURE:
<223> OTHER INFORMATION: Target sequence

<400> SEQUENCE: 20
acctacccga gcggctg                                                  17

<210> SEQ ID NO 21
<211> LENGTH: 13
<212> TYPE: DNA
<213> ORGANISM: Artificial sequence
<220> FEATURE:
<223> OTHER INFORMATION: Probe sequence

<400> SEQUENCE: 21
cgctgccgca cac                                                      13

<210> SEQ ID NO 22
<211> LENGTH: 13
<212> TYPE: DNA
<213> ORGANISM: Artificial sequence
<220> FEATURE:
<223> OTHER INFORMATION: Target sequence

<400> SEQUENCE: 22
gtgtgcggca gcg                                                      13

<210> SEQ ID NO 23
<211> LENGTH: 25
<212> TYPE: DNA
<213> ORGANISM: Artificial sequence
<220> FEATURE:
<223> OTHER INFORMATION: PCR primer

<400> SEQUENCE: 23
gcacaagcca tatttaagca gaaac                                         25

<210> SEQ ID NO 24
<211> LENGTH: 25
<212> TYPE: DNA
<213> ORGANISM: Artificial sequence
<220> FEATURE:
<223> OTHER INFORMATION: Target sequence

<400> SEQUENCE: 24
gtttctgctt aaatatggct tgtgc                                         25

<210> SEQ ID NO 25
<211> LENGTH: 25
<212> TYPE: DNA
<213> ORGANISM: Artificial sequence
<220> FEATURE:
<223> OTHER INFORMATION: PCR primer

<400> SEQUENCE: 25
aactccatat aagggcacac aagtc                                         25

<210> SEQ ID NO 26
<211> LENGTH: 25
<212> TYPE: DNA
<213> ORGANISM: Artificial sequence
<220> FEATURE:
<223> OTHER INFORMATION: Target sequence

<400> SEQUENCE: 26
gacttgtgtg cccttatatg gagtt                                         25
```

```
<210> SEQ ID NO 27
<211> LENGTH: 16
<212> TYPE: DNA
<213> ORGANISM: Artificial sequence
<220> FEATURE:
<223> OTHER INFORMATION: Probe sequence

<400> SEQUENCE: 27
ctccgtctcc tgcaac                                                      16

<210> SEQ ID NO 28
<211> LENGTH: 16
<212> TYPE: DNA
<213> ORGANISM: Artificial sequence
<220> FEATURE:
<223> OTHER INFORMATION: PCR sequence

<400> SEQUENCE: 28
gttgcaggag acggag                                                      16
```

METHOD FOR DETECTION OF MELANOMA

CROSS REFERENCE TO RELATED APPLICATIONS

This application claims priority under 35 U.S.C. § 119(e) to Provisional Application Ser. No. 60/302,348, filed Jun. 28, 2001, which is incorporated herein by reference in its entirety.

FIELD OF THE INVENTION

This invention relates to methods related to melanoma patient for detecting expression of genes in a skin sample of the epidermis related to malignant melanoma.

BACKGROUND OF THE INVENTION

Malignant melanoma ranks second among adult cancers (behind adult leukemia) in potential years of life lost. Each year, over 47,000 new cases are diagnosed, and the incidence of cutaneous melanoma appears to be rising rapidly. Treatment of malignant melanoma involves surgical excision of the primary lesion, and vigilant monitoring to detect recurrence. Currently, there is no approved therapy for patients having intermediate risk of relapse. High-dose interferon, which can have serious side effects, is approved for treatment of patients having high-risk melanoma. There is no cure at this time for patients in whom metastasis to distant sites has occurred.

Dermatologists recommend that early detection of melanoma is the only way to reduce melanoma mortality by identifying curable lesions (Weinstock, *JAMA* 284:886-889, 2000). In practice, suspicious lesions are biopsied or excised, and examined by histology. Clinical suspicion, however, largely depends on the experience and the skills of the examining doctor. Very often the number of nevi under suspicion by far exceeds the number of lesions that could be removed. Erroneously excised lesions are costly for the public and cause scars often in cosmetically important body regions. A non-invasive molecular tool for diagnosis is therefore desirable. Furthermore, even after a lesion is taken out differentiation of benign melanocytic lesions from melanomas can be very difficult in a subset of about 10-15%, even for skilled dermatopathologists. If the diagnosis melanoma is made, tumor thickness is among the most important factors to roughly evaluate the prognosis of a melanoma patient (Breslow, *Ann. Surg.* 172:902-908, 1970). Molecular markers that could reflect the prognosis more precisely have also not been established. In addition, histological examination of cancer cells does not adequately reflect the complicated series of molecular events underlying the neoplastic process. Consequently, research efforts are now being focused on molecular profiling of cancer cells using DNA array technology, in which the activity of many genes or proteins are studied in parallel. Molecular profiling of human cancer has been recently reviewed (Liotta and Petricoin, *Nature Reviews/Genetics* 1:48-56, 2000).

Several approaches have been taken to simplify the analysis of gene expression profiles in tissue samples. Cell strains have been cultured to focus on a specific cell of interest. For example, some melanoma cell lines appear to accurately represent the original primary material (Bittner et al 2000). However, cultured cells lack the regulatory elements contributed by neighboring cells that affect gene expression in vivo, such as cell-cell communication molecules, soluble factors, and extracellular matrix molecules.

More direct methods for gene expression profiling of cellular subtypes include the global survey approach and microdissection. In the global approach, the information content of interacting cells is preserved by extracting RNA directly from a heterogeneous piece of tissue. To normalize the data set for the actual abundance of normal tissue, in relation to what is often minor amounts of diseased tissue, a reference gene set is constructed using RNA profiles extracted from a particular subtype of cultured cells. Preservation of mRNA in tissue samples in the clinical setting is challenging, since RNA is very labile and is susceptible to abundant tissue RNases (Liotta and Petricoin, *Nature Reviews/Genetics* 1:48-56, 2000).

An alternative approach, microdissection, utilizes mechanical force or laser capture methods to select a cellular subtype from a tissue sample, for subsequent molecular profiling. Transition stages from normal cells through carcinoma in situ, to invasive cancer can be identified microscopically, and profiled with microdissection techniques to discover molecular events occurring along the progression to malignancy. A disadvantage to this approach is the level of expertise and instrumentation required to select the pathological cells from the biopsied tissue sample.

Therefore, there remains a need for effective methods to detect malignant melanoma and to diagnose and stage melanoma from a suspicious skin lesion.

SUMMARY OF THE INVENTION

The present specification discloses markers for early and late stage malignant melanoma, and methods for detecting these markers using non-invasive sampling procedures. Accordingly, the present invention provides methods for detecting, staging, monitoring, diagnosing, prognosing and assisting in the management of malignant melanoma by analyzing a skin sample for gene expression. For example, in one aspect, mRNAs of at least one of IL-1 RI, endothelin-2, ephrin-A5, IGF Binding Protein 7, HLA-A0202 heavy chain, Activin A (βA subunit), TNF RII, SPC4, and CNTF Rα are detected. In certain preferred embodiments, the skin sample is a human skin sample from a lesion suspected of being melanoma.

In one aspect, the present invention provides a non-invasive method for detecting malignant melanoma in a skin sample of a subject, typically a human subject. The method includes analyzing expression in the skin sample, of one or more melanoma skin markers. The melanoma skin markers include, but are not limited to, IL-1 RI, endothelin-2, ephrin-A5, IGF Binding Protein 7, HLA-A0202 heavy chain, Activin A (βA subunit), TNF RII, SPC4, and CNTF Rα. The melanoma skin markers exhibit different expression levels in a skin sample at the site of a melanoma compared to levels in a skin sample at the site of a benign lesion.

In one embodiment, the skin sample is obtained by applying at least one application of an adhesive to the skin and removing the adhesive from the skin, or scraping the skin with an instrument to remove a sample comprising a nucleic acid from the skin. Typically, nucleic acids, preferably ribonucleic acids (RNA), most preferably messenger RNA (mRNA) from the skin sample are analyzed.

In a preferred embodiment, the method includes analyzing nucleic acids of the skin sample for expression levels of IL-1 RI, endothelin-2, ephrin-A5, IGF Binding Protein 7, HLA-A0202 heavy chain, Activin A (βA subunit), TNF RII, SPC4, and CNTF Rα. In this embodiment, expression levels of the IL-1 RI, endothelin-2, and ephrin-A5 are related to early stage melanoma, and expression levels of IGF Binding Protein 7, HLA-A0202 heavy chain, Activin A (βA subunit), TNF RII, SPC4, and CNTF Rα are related to late stage melanoma. More particularly, an increase in the expression levels of IGF Binding Protein 7, HLA-A0202 heavy chain, Activin A (βA subunit), TNF RII, SPC4, and CNTF Rα are related to late stage melanoma. Furthermore, an increase in the expression levels of endothelin-2, and ephrin-A5 genes are related to early stage melanoma. Finally, a decrease in levels of IL-1 RI are related to early stage melanoma.

In another aspect, the present invention provides a non-invasive method for staging malignant melanoma in a subject skin sample. The method includes analyzing expression in a nucleic acid sample of one or more melanoma skin markers. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. Expression of the melanoma skin markers is related to melanoma.

In another aspect, the present invention provides a non-invasive method for staging malignant melanoma in a skin sample from a human subject. The method includes obtaining a skin sample by applying an adhesive surface to the skin and removing the adhesive surface from the skin such that a skin sample comprising nucleic acid in an amount sufficient for subsequent detection adheres to the adhesive surface after its removal. Then, analyzing expression of melanoma skin markers in nucleic acids of the skin sample. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. In this aspect, expression of the IL-1 RI, endothelin-2, and ephrin-A5 is related to early stage melanoma, and expression of IGF Binding Protein 7, HLA-A0202 heavy chain, Activin A (βA subunit), TNF RII, SPC4, and CNTF Rα is related to late stage melanoma.

In another aspect, the present invention provides a non-invasive method for monitoring a suspicious lesion of a subject. The method includes analyzing expression of one or more melanoma skin markers in a skin sample taken from the suspicious lesion at a first time point and a second time point, and comparing the expression at the first time point and the second time point. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. Expression of the melanoma skin markers is related to melanoma, such that a change in the expression of one or more of the melanoma skin markers over time is indicative of melanoma. In certain preferred embodiments, the skin sample includes nucleic acids, and is a human skin sample.

In another aspect, the present invention provides a non-invasive method for detecting expression of IL-1 RI, endothelin-2, ephrin-A5, IGF Binding Protein 7, HLA-A0202 heavy chain, Activin A (βA subunit), TNF RII, SPC4, and CNTF Rα genes in a skin sample. The method includes obtaining a skin sample by applying an adhesive surface to the skin and removing the adhesive surface from the skin such that a skin sample comprising nucleic acid in an amount sufficient for subsequent detection adheres to the adhesive surface after its removal. Then, analyzing expression of IL-1 RI, endothelin-2, ephrin-A5, IGF Binding Protein 7, HLA-A0202 heavy chain, Activin A (βA subunit), TNF RII, SPC4, and CNTF Rα in the nucleic acids of the skin sample. Typically, for this aspect of the invention, mRNA from the skin sample are the analyzed nucleic acids.

In another aspect the present invention provides a kit for detecting malignant melanoma. The kit includes one or more probes or primers that selectively bind to one or more of Interleukin-1 RI (IL-1 RI), endothelin-2, ephrin-A5, Insulin-like Growth Factor (IGF) Binding Protein 7, Human Leukocyte Antigen (HLA)-A0202 heavy chain, Activin A (βA subunit), Tumor Necrosis Factor (TNF) RII, SPC4, and Ciliary Neurotrophic Factor (CNTF) Rα. The kit can include a skin sample collection device, such as an adhesive strip.

DETAILED DESCRIPTION OF THE INVENTION

Figure 1:
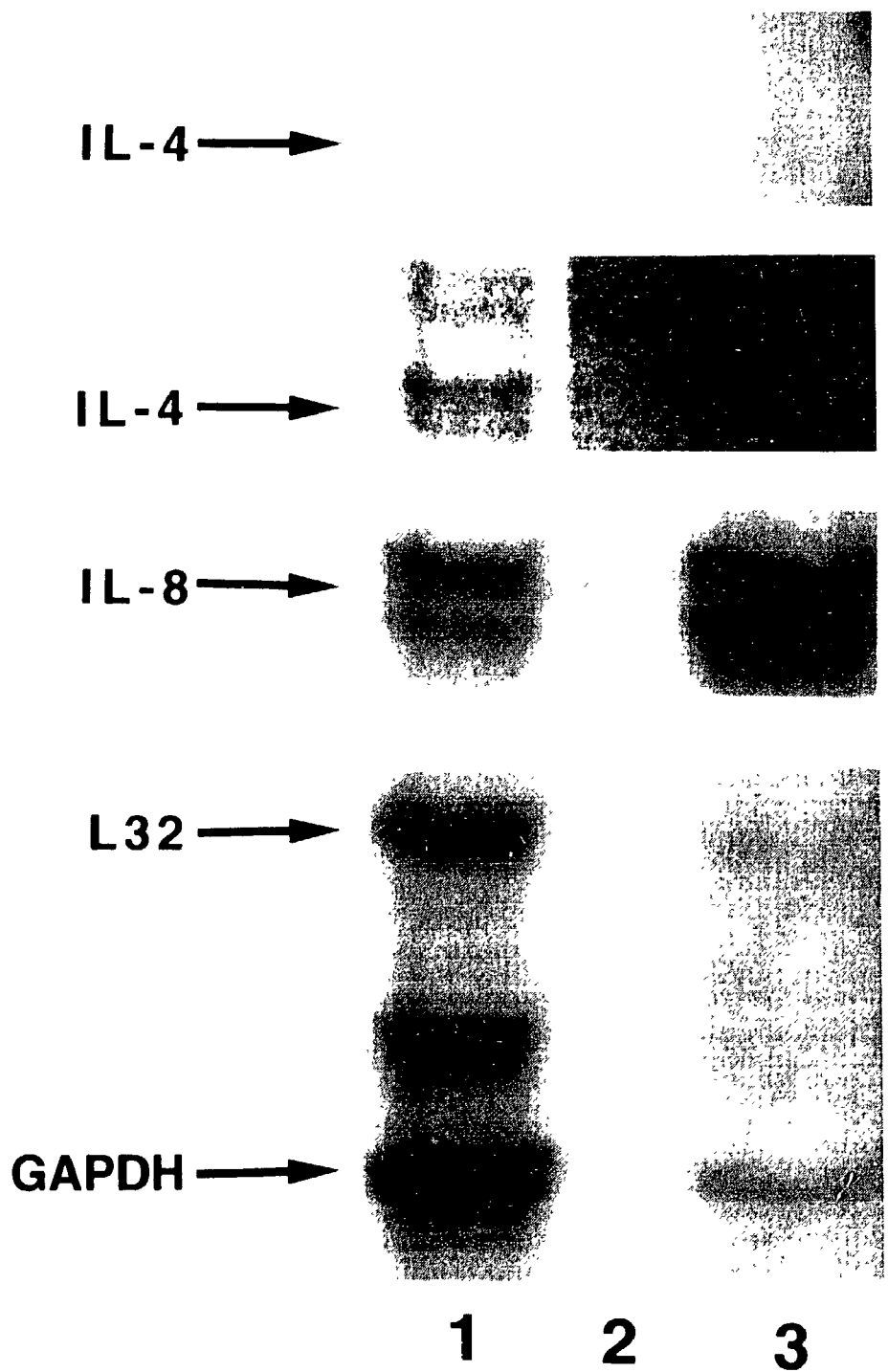
FIG. 1 is an exposure of a gel representing the results for ribonuclease protection assay (RPA) performed with RNA obtained by tape stripping three different areas of the upper arms of the same subject. Each of the three sites were stripped 12 times. Four different RNA probes (IL-4, IL-8, L32, GADPH) were used for hybridization to RNA samples obtained from the subject. Lane 1 shows the RNA isolated from an erythematous area of skin, read clinically as 2+ erythema that was induced by squarate (ACD). Shown in lane 3 is the RNA isolated from an ICD erythematous site (scored 2+) induced by 0.5% sodium lauryl sulfate (SLS). Both lanes demonstrate a band for IL-8. Lane 2 represents sample obtained from non-inflamed, normal appearing skin of the same subject. A band for the cytokine, IL-4, can be seen in lane 1 which was derived from an allergic reaction.

In one aspect, the present invention provides a non-invasive method for detecting malignant melanoma in a skin sample of a subject. The method includes analyzing expression in skin sample of one or more melanoma skin markers. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. Expression of the melanoma skin markers is related to melanoma. In certain preferred embodiments, the skin sample includes nucleic acids, and is a human skin sample from a lesion suspected of being melanoma.

In another aspect, the present invention provides a non-invasive method for staging malignant melanoma in a skin sample of a human subject. The method includes analyzing expression in the skin sample of one or more melanoma skin markers. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. Either an increase or a decrease in expression of the melanoma skin markers, is related to melanoma. In certain preferred embodiments, expression is analyzed by analyzing mRNAs of one or more skin markers from the skin sample, and is a human skin sample from a lesion suspected of being melanoma.

In a preferred embodiment, the method includes analyzing expression in the skin sample by measuring expression levels of IL-1 RI, endothelin-2, ephrin-A5, IGF Binding Protein 7, HLA-A0202 heavy chain, Activin A (βA subunit), TNF RII, SPC4, and CNTF Rα mRNAs. Expression levels of the IL-1 RI, endothelin-2, and ephrin-A5 genes are related to early stage melanoma, and expression levels of the genes for IGF Binding Protein 7, HLA-A0202 heavy chain, Activin A (βA subunit), TNF RII, SPC4, and CNTF Rα are related to late stage melanoma. More particularly, an increase in the expression levels of IGF Binding Protein 7, HLA-A0202 heavy chain, Activin A (βA subunit), TNF RII, SPC4, and CNTF Rα are related to late stage melanoma. Furthermore, an increase in the expression levels of endothelin-2, and ephrin-A5 genes are related to early stage melanoma. Finally, a decrease in levels of IL-1 RI are related to early stage melanoma. The method can include the combination of all of the melanoma skin markers, or all of the early stage melanoma skin markers, or all of the late-stage melanoma skin markers, weighted according to F-power in a multivariate analysis, to increase the accuracy of the method.

In another preferred embodiment, the method includes detecting expression of IL-1 RI, endothelin-2, and ephrin-A5 to detect malignant melanoma in patients at risk for developing malignant melanoma. These genes are identified herein as being differentially expressed in early-stage melanoma. In another preferred embodiment, the method includes detecting expression of endothelin-2 and ephrin-A5.

The method for detecting malignant melanoma, may be a molecular diagnostic screening test for early melanoma that includes analyzing mRNAs of the markers IL-1 RI, endothelin-2, and ephrin-A5 in nucleic acids, typically RNA extracted from a skin sample of a patient population, such as those at risk for developing malignant melanoma due to a family history of malignant melanoma. The sample is preferably obtained using a non-invasive skin surface sampling method, as described herein. The methods for detecting malignant melanoma of the present invention, can serve as aids for initial therapeutic decisions, saving many lives and reducing the cost of this safety by avoiding unnecessary excisions and biopsies.

The methods of the present invention are particularly useful in the family practice setting for managing patients at risk for developing melanoma. For example, the methods are useful in the following patient groups: a) patients with multiple moles, especially when excisions of all suspected moles can not be performed or suspicious lesions reside in cosmetically problematical body parts, e.g. the face, the breast, and décolleté in females etc.; b) patients with dysplastic nevus syndrome at higher risk to get melanoma, c) patients who have suffered from primary melanoma, and therefore are at increased risk to get a second one; and d) patients with familial risk (i.e. genetic predisposition) for melanoma.

The methods of the present invention use a non-invasive method to obtain a sample of skin from a subject suspected of having melanoma or at increased risk of developing melanoma. In certain preferred embodiments, the skin sample is a human skin sample from a lesion suspected of being melanoma. In preferred embodiments, the skin sample includes nucleic acids, which can then be analyzed using methods such as, but not limited to, those described below. Levels of melanoma skin markers can be quantitated in the sample by measuring their absolute or relative expression at the protein or preferably RNA levels, and comparing these levels to those of normal, control samples. As illustrated in Example 4 herein, information regarding expression of malignant melanoma skin markers disclosed herein, provides information regarding the presence and the stage of malignant melanoma. A decrease in expression levels of IL-1 RI and/or an increase in expression levels of endothelin-2 and/or ephrin-A5 is indicative of early stage melanoma. An increase in expression levels of IGF Binding Protein 7, HLA-A0202 heavy chain, Activin A (βA subunit), TNF RII, SPC4, and/or CNTF Rα is indicative of late stage melanoma.

It will be recognized that the non-invasive sample is typically taken from below the stratum corneum of the skin. As illustrated in Example 4, by using the methods of the invention it is possible to detect and stage malignant melanoma by analyzing the melanoma skin markers disclosed herein.

In one embodiment, expression is analyzed for at least one of IL-1 RI, endothelin-2, and ephrin-A5. In another embodiment, expression is analyzed for at least two, or all, of IL-1 RI, endothelin-2, and ephrin-A5. In another embodiment, expression is analyzed for one or both of endothelin-2 and ephrin-A5. In another embodiment, expression is analyzed for at least one of IGF Binding Protein 7, HLA-A0202 heavy chain, Activin A (βA subunit), TNF RII, SPC4, and CNTF Rα. In another embodiment, expression is analyzed for IGF Binding Protein 7, HLA-A0202 heavy chain, Activin A (βA subunit), TNF RII, SPC4, and CNTF Rα. In another embodiment, expression is analyzed for at least one of IGF Binding Protein 7, HLA-A0202 heavy chain, Activin A (βA subunit), TNF RII, SPC4, and CNTF Rα. In another embodiment, expression is analyzed for at least one of endothelin-1, ephrin-A5, IGF Binding Protein 7, HLA-A0202 heavy chain, Activin A (βA subunit), TNF RII, SPC4, and CNTF Rα.

A "melanoma skin marker" is a gene whose expression level is different between skin surface samples at the site of malignant melanoma and skin surface samples of normal skin or a lesion, which is benign, such as a benign nevus. Therefore, expression of a melanoma skin marker is related to, or indicative of, melanoma. As discussed herein, all of the melanoma skin markers of the present invention exhibit increased expression in melanoma cells as compared to benign nevi, except for IL1 RI. Many statistical techniques are known in the art, which can be used to determine whether a statistically significant difference in expression is observed at a 90% or preferably a 95% confidence level. Example 4 illustrates the use of a statistical test to identify melanoma skin markers. An increase or decrease in expression of these genes is related to malignant melanoma. In certain preferred embodiments, there is at least a two-fold difference in levels between skin sample near the site of malignant melanoma and skin samples from normal skin.

Melanoma skin markers identified herein include Interleukin-1 Receptor (IL-1 RI) (Genbank accession number X16896, Human mRNA for interleukin-1 receptor); Endothelin-2 (Genbank accession number M65199, Human endothelin 2 (ET2) mRNA); Ephrin-A5 (Genbank accession number U26403, Human receptor tyrosine kinase ligand LERK-7 precursor (EPLG7) mRNA); Insulin-like Growth Factor (IGF) Binding Protein 7 (Genbank accession number L19182, Human MAC25 mRNA); Human Leukocyte Antigen (HLA)-A0202 heavy chain (Genbank accession number M84379, Human MHC class I lymphocyte antigen (HLA-A 0201) mRNA); Activin A (βA subunit) (Genbank accession number M13436, Human ovarian beta-A inhibin mRNA); Tumor Necrosis Factor (TNF) RII (Genbank accession number M55994, Human tumor necrosis factor receptor II (TNFrII) mRNA); SPC4 (Genbank accession number M80482, Human subtilisin-like protein (PACE4) mRNA); and Ciliary Neurotrophic Factor (CNTF) Rα (Genbank accession number M73238, Human ciliary neurotrohic factor receptor (CNTFR) mRNA). One of ordinary skill in the art recognizes that Genbank accession numbers refer to numbers used to identify nucleotide sequences available in Genbank (Benson et al., "GenBank," *Nucleic Acids. Res.* 30(1): 17-20 (2002)).

As used herein, the terms "nucleic acid," "polynucleotide," or "nucleic acid sequence" refer to a polymer of deoxyribonucleotides or ribonucleotides, in the form of a separate fragment or as a component of a larger construct. Polynucleotide or nucleic acid sequences of the invention include DNA, RNA, including mRNA and cDNA sequences. The polynucleotides of the sample of the present invention are typically RNA.

As used herein, the term "polypeptide" refers to a polymer of amino acid residues in the form of a separate fragment or component of a larger construct. An example of a polypeptide includes amino acid sequences encoding a cytokine or fragments thereof. A polypeptide may encode for a functional protein or fragments of a protein. For example, an endothelin-2 polypeptide includes the full-length protein sequence of endothelin-2 as well as fragments thereof consisting of a polymer of amino acids.

In a preferred embodiment, the skin sample is obtained by applying at least one application of an adhesive to the skin and removing the adhesive from the skin, or by scraping the skin with an instrument to remove a sample comprising a nucleic acid from the skin. The skin sample can be obtained by using a tape stripping methodology in which one or more tape strips are applied to the same skin site. Methods for non-invasively obtaining a skin sample are discussed in U.S. patent application Ser. No. 09/375,609, filed Aug. 17, 1999, incorporated herein by reference.

The skin sample can be obtained by applying the adhesive surface to the skin between 1 and 50 times, preferably between 1 and 25 times. In certain preferred embodiments, the adhesive surface is applied to the skin between 1 and 3, most preferably between 1 and 2 times, to obtain the skin sample. Using a preferred non-invasive sampling method, such as a tape-stripping methodology, the sample is obtained in a manner such that the skin nucleic acid profile after application is not affected for up to about one hour, and typically for up to two hours.

Skin samples obtained on adhesive films can be frozen before being analyzed using the methods of the present invention. Typically, this is performed by snap-freezing a sample, as illustrated in Example 4, using liquid nitrogen or dry ice.

The term "skin" means a tissue comprising a sheet of cells, one or several layers thick, organized above a basal lamina, and often specialized for mechanical protection or active transport. In a preferred embodiment, the skin is mammalian skin. In a more preferred embodiment the skin is human skin.

The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

In preferred embodiments of the present invention, the skin sample includes epidermal cells. The epidermis consists predominantly of keratinocytes (>90%), which differentiate from the basal layer, moving outward through various layers having decreasing levels of cellular organization, to become the cornified cells of the stratum corneum layer. Renewal of the epidermis occurs every 20-30 days in normal skin. Other cell types present in the epidermis include melanocytes, Langerhans cells, and Merkel cells. Preferably, the skin sample of the methods of the present invention is an epidermis skin sample.

The term "sample" refers to any preparation derived from skin of a subject. For example, a sample of cells obtained using the non-invasive method described above may be used to isolate polynucleotides, polypeptides, or lipids, preferably polynucleotides and polypeptides, most preferably polynucleotides, for the methods of the present invention. In addition, the methods of the invention can be used in vitro, for example with skin cells cultured on a solid or semi-solid support and organotypic skin constructs. In such instances, the skin cells may be from any source suspected of being melanoma or from an individual at risk of developing melanoma.

Samples for the present invention, typically are taken from a mole, or from another type of suspicious lesion (i.e. lesion suspected of being melanoma), especially one that resides in cosmetically problematical body parts, e.g. the face, the breast, décolleté in females, etc. The samples are taken of the skin surface of the suspicious lesion using non-invasive skin sampling methods discussed herein.

A "skin lesion" is a change in the color or texture in an area of skin. "Skin lesions suspected of being melanoma" are skin lesions with characteristics of malignant melanoma, which are well known to dermatologists and oncologists. Such lesions are sometimes raised and can have a color that is different from the color of normal skin of an individual (e.g. brown, black, red, or bluish). Lesions suspected of being melanoma sometimes include a mixture of colors, are often asymmetrical, can change in appearance over time, and may bleed. A skin lesion suspected of being melanoma may be a mole or nevus. Melanoma lesions are usually, but not always, larger than 6 mm in diameter. Melanoma includes superficial spreading melanoma, nodular melanoma, acral lentiginous melanoma, and lentigo-maligna melanoma. Melanoma can occur on skin that has been overexposed to the sun. Therefore, in one embodiment the skin sample is taken from an area of skin that has been overexposed to the sun.

Typically, prior to the present invention a skin biopsy and histological examination was used to confirm diagnosis of a lesion as malignant melanoma. Furthermore, an X-ray, CT scan, MRI, or other procedures are sometimes indicated to determine if spreading (metastasis) has occurred. Such methods could be used in conjunction with the present invention, or could be eliminated as a result of the present invention.

The methods of the present invention which detect the melanoma skin markers identified herein have utility not only in detecting and staging a skin sample from a mole or other lesion suspected of being melanoma, but also in diagnosing, and prognosing malignant melanoma.

Samples from a tissue can be isolated by any number of means well known in the art. Invasive methods for isolating a sample include the use of needles, for example during blood sampling, as well as biopsies of various tissues. Due to the invasive nature of these techniques there is an increased risk of mortality and morbidity. The methods and kits of the present invention typically use a non-invasive sampling method to obtain a skin sample.

Methods of the present invention can include a rapid, non-invasive skin-sampling method for obtaining polynucleotides, typically RNA, preferably mRNA. The process of tape stripping itself has been shown not to affect the skin cytokine profile during the first two hours after the procedure is done.

A non-invasive sampling method can include scraping epidermal cells of the skin with a rigid instrument. The instrument can be, for example, a sterile #15 scalpel. However, it will be recognized that any number of rigid instruments capable of removing only the surface layer (i.e., stratum corneum) of the skin may be used. Alternatively, instead of scraping the skin, the skin's epidermal layer may be removed by using an adhesive surface, such as, but not limited to an adhesive tape, for example, but not limited to, Duct tape (333 Duct tape, Nashua tape products), Scotch® tape (3M Scotch 810, St. Paul, Minn.), or a similar adhesive product. A preferred, but non-limiting example of an adhesive tape is D-SQUAME® (CuDerm, Dallas, Tex.).

In this embodiment the skin is stripped with the tape and the stripped cells and cellular material are then recovered from the scalpel, tape or other item. For example, tape used to obtain skin cells and cellular material can be centrifuged in a sterile microfuge tube containing lysis buffer. In the case of the scalpel the cells and cellular material can be transferred to a sterile Petri dish and any cells present lysed therein with lysis buffer. The same lysis buffer may be reused for each piece of tape or scalpel used at a single skin site. For certain applications, the tape stripping method can be combined with the scraping method for removing cells and cellular material from the skin. The sample obtained can then be further processed, for example to isolate nucleic acids, polypeptides, or lipids. Preferably, the method utilized does not adversely affect the polynucleotide, polypeptide, or lipid level being measured.

Polynucleotides can be isolated from the lysed cells and cellular material by any number of means well known to those skilled in the art. For example, a number of commercial products are available for isolating polynucleotides, including but not limited to, TriReagent (Molecular Research Center, Inc, Cincinnati, Ohio) can be used. The isolated polynucleotides can then be tested or assayed for particular nucleic acid sequences, including a polynucleotide encoding a cytokine.

Expression of melanoma skin markers is analyzed in the methods of the present invention. Analyzing expression includes any qualitative or quantitative method for detecting expression of a gene, many of which are known in the art. The method can include analyzing expression of the melanoma skin markers by measuring expression of the melanoma skin markers using a quantitative method, or by using a qualitative method. Non-limiting methods for analyzing polynucleotides and polypeptides are discussed below. Preferably, expression is analyzed using methods that are directed to polynucleotides.

The methods of analyzing expression of a malignant melanoma of the present invention can utilize a biochip, or other miniature high-throughput technology, for detecting expression of two or more malignant melanoma skin markers. As illustrated in Example 4, the manufacture and use of biochips such as those involving bioarrays, are known in the art and commercially available (See e.g., bioarrays available from Sigma-Genosys (The Woodlands, Tex.); Affymetrix (Santa Clara, Calif.), and Full Moon Biosystems (Sunnyvale, Calif.)) (For reviews of Biochips and bioarrays see, e.g., Kallioniemi O. P., "Biochip technologies in cancer research," *Ann Med*, March; 33(2):142-7 (2001); and Rudert F., "Genomics and proteomics tools for the clinic," Curr Opin. Mol. Ther., December; 2(6):633-42 (2000)).

Such bioarrays can be analyzed using blotting techniques similar to those discussed below for conventional techniques of detecting polynucleotides and polypeptides, as illustrated in Example 4. Other microfluidic devices and methods for analyzing gene expression, especially those in which more than one gene can be analyzed simultaneously and those involving high-throughput technologies, can be used for the methods of the present invention.

Quantitative measurement of expression levels using bioarrays is also known in the art, and typically involve a modified version of a traditional method for measuring expression as described herein. For example, such quantitation can be performed by measuring a phosphor image of a radioactive-labeled probe binding to a spot of a microarray, using a phosphor imager and imaging software.

The method of the present invention typically employ RNA, including messenger RNA (mRNA), isolated from a skin sample. The RNA may be single stranded or double stranded. Enzymes and conditions optimal for reverse transcribing the template to DNA well known in the art can be used. Alternatively, the RNA can be subjected to RNAse protection assays. A DNA-RNA hybrid that contains one strand of each can also be used. A mixture of polynucleotides can also be employed, or the polynucleotides produced in a previous amplification reaction, using the same or different primers may be so used. In the instance where the polynucleotide sequence is to be amplified the polynucleotide sequence may be a fraction of a melanoma skin marker, or can be present initially as a discrete molecule, such that the specific sequence is the entire nucleic acid. It is not necessary that the sequence to be amplified be present initially in a pure form; it may be a minor fraction of a complex mixture.

In addition, RNAse protection assays can be used if RNA is the polynucleotide obtained from the sample. In this procedure, a labeled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a ribonucleotide capable of hybridizing to RNA in a sample of interest. Those skilled in the art will be able to identify and modify the RNAse protection assay specific to the polynucleotide to be measured, for example, probe specificity may be altered, hybridization temperatures, quantity of nucleic acid etc. Additionally, a number of commercial kits are available, for example, RiboQuant™ Multi-Probe RNAse Protection Assay System (Pharmingen, Inc., San Diego, Calif.).

In another embodiment, the polynucleotide in the sample may be analyzed by a blotting procedure, typically a Northern blot procedure. For blotting procedures polynucleotides are separated on a gel and then probed with a complementary polynucleotide to the sequence of interest. For example, RNA is separated on a gel transferred to nitrocellulose and probed with complementary DNA to one of the melanoma differentially-diagnosed genes disclosed herein. The complementary probe may be labeled radioactively, chemically etc. Hybridization of the probe is indicative of the presence of the melanoma of interest.

Detection of a polynucleotide encoding a melanoma skin marker can be performed by standard methods such as size fractionating the nucleic acid. Methods of size fractionating the DNA and RNA are well known to those of skill in the art, such as by gel electrophoresis, including polyacrylamide gel electrophoresis (PAGE). For example, the gel may be a denaturing 7 M or 8 M urea-polyacrylamide-formamide gel. Size fractionating the nucleic acid may also be accomplished by chromatographic methods known to those of skill in the art.

The detection of polynucleotides may optionally be performed by using radioactively labeled probes. Any radioactive label may be employed which provides an adequate signal. Other labels include ligands, colored dyes, and fluorescent molecules, which can serve as a specific binding pair member for a labeled ligand, and the like. The labeled preparations are used to probe for a polynucleotide by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see *Genetic Engineering*, 1 ed. Robert Williamson, Academic Press (1981), pp. 72-8 1). The particular hybridization technique is not essential to the invention. Hybridization techniques are well known or easily ascertained by one of ordinary skill in the art. As improvements are made in hybridization techniques, they can readily be applied in the method of the invention.

Probes according to the present invention and used in a method of the present invention selectively hybridize to the melanoma skin markers disclosed herein. In preferred embodiments, the probes are spotted on a bioarray using methods known in the art. As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in detecting expression of a melanoma skin marker. It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule.

Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)). An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42 EC (moderate stringency conditions); and 0.1×SSC at about 68 EC (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The polynucleotides encoding melanoma skin markers may be amplified before they are detected. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the method of the invention is not to be limited to the embodiments of amplification described herein.

One method of in vitro amplification, which can be used according to this invention, is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the presence of polynucleotides encoding cytokines in the sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° for 5 min. For another example, DNA can be subjected to 35 polymerase chain reaction cycles in a thermocycler at a denaturing temperature of 95° C. for 30 sec, followed by varying annealing temperatures ranging from 54-58° C. for 1 min, an extension step at 70° C. for 1 min and a final extension step at 70° C.

The primers for use in amplifying the polynucleotides of the invention may be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of nucleotide sequence to be amplified. The term "complementary" means that the primers must hybridize with their respective strands under conditions, which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementarity with the complementary flanking strand.

Primers and probes for the differentially expressed melanoma skin markers of the present invention, can be developed using known methods combined with the present disclosure. For example, but not intended to be limiting, PCR primers for IL1 RI can include:
Forward: TTCAGGACATTACTATTGCG (SEQ ID NO:1)
(Target CGCAATAGTAATGTCCTGAA (SEQ ID NO:2)
Reverse: TTCCACACTGTAATAGTCTTC (SEQ ID NO:3)
(Target GAAGACTATTACAGTGTGGAA (SEQ ID NO:4)

Another non-limiting example of primers and probes of the present invention, are primers and probes that selectively hybridize to the target sequences identified above (SEQ ID NOS:2 and 4).

Those of ordinary skill in the art will know of various amplification methodologies that can also be utilized to increase the copy number of target nucleic acid. The polynucleotides detected in the method of the invention can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., *Bio/Technology* 3:1008-1012 (1985)), allele-specific oligonucleotide (ASO) probe analysis (Conner et al., *Proc. Natl. Acad. Sci. USA* 80: 278 (1983), oligonucleotide ligation assays (OLAs) (Landegren et al., *Science* 241:1077 (1988)), RNAse Protection Assay and the like. Molecular techniques for DNA analysis have been reviewed (Landegren et al, *Science* 242: 229-237 (1988)). Following DNA amplification, the reaction product may be detected by Southern blot analysis, without using radioactive probes. In such a process, for example, a small sample of DNA containing the polynucleotides obtained from the tissue or subject are amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

The methods of the present invention can involve a real-time quantitative PCR assay, such as a Taqman® assay (Holland et al., *Proc Natl Acad Sci USA*, 88(16):7276 (1991)). The assays can be performed on an instrument designed to perform such assays, for example those available from Applied Biosystems (Foster City, Calif.). Primers and probes for such an assay can be designed according to known procedures in the art. For example, primers and probes for some of the differentially expressed melanoma skin markers of the present invention can include, but are not limited to, the following:

Endothelin 2
Forward CTGCCAAGGCGCTGTCA (SEQ ID NO:5)
(Target: TGACAGCGCCTTGGCAG)(SEQ ID NO:6)
Reverse TCAGTCCAGGGCCTTCGA (SEQ ID NO:7)
(Target: TCGAAGGCCCTGGACTGA) (SEQ ID NO:8)
Probe TGCCAGGGACCCC (SEQ ID NO:9)
(Target: GGGGTCCCTGGCA) (SEQ ID NO:10)
Inhibin (Activin)
Forward AACATGCTGCACTTGAAGAAGAGA (SEQ ID NO:11)
(Target: TCTCTTCTTCAAGTGCAGCATGTT) (SEQ ID NO:12)
Reverse GAAGCTTTCTGATCGCGTTCA (SEQ ID NO:13)
(Target: TGAACGCGATCAGAAAGCTTC) (SEQ ID NO:14)
Probe CCGGCTGGGTGACAT (SEQ ID NO:15)
(Target: ATGTCACCCAGCCGG) (SEQ ID NO:16)
InsulinBindingProtein7
Forward GCGTGTGCGTGTGCAAGA (SEQ ID NO:17)
(Target: TCTTGCACACGCACACGC) (SEQ ID NO:18)
Reverse CAGCCGCTCGGGTAGGT (SEQ ID NO:19)
(Target: ACCTACCCGAGCGGCTG) (SEQ ID NO:20)
Probe CGCTGCCGCACAC (SEQ ID NO:21)
(Target: GTGTGCGGCAGCG) (SEQ ID NO:22)
ILIR1
Forward GCACAAGCCATATTTAAGCAGAAAC (SEQ ID NO:23)

(Target: GTTTCTGCTTAAATATGGCTTGTGC) (SEQ ID NO:24)
Reverse AACTCCATATAAGGGCACACAAGTC (SEQ ID NO:25)
(Target: GACTTGTGTGCCCTTATATGGAGTT) (SEQ ID NO:26)
Probe CTCCGTCTCCTGCAAC (SEQ ID NO:27)
(Target: GTTGCAGGAGACGGAG) (SEQ ID NO:28)

Another non-limiting example of primers and probes of the present invention, are primers and probes that selectively hybridize to the target sequences identified above (SEQ ID NOS:6, 8, 10, 12, 14, 16, 18, 20, 22, 24, 26, and 28).

Simple visualization of a gel containing the separated products may be utilized to analyze the melanoma skin markers according to the methods of the present invention. For example, staining of a gel to visualize separated polynucleotides, a number of stains are well known to those skilled in the art. However, other methods known to those skilled in the art may also be used, for example scanning densitometry, computer aided scanning and quantitation as well as others.

The method for detecting one or more melanoma skin markers may alternatively employ the detection of a polypeptide product of one of these genes. The method for detecting a polypeptide derived from a melanoma skin marker in cells is useful for detecting melanoma by measuring the level of one or more melanoma skin marker product, for example IL-1 RI, endothelin-2, ephrin-A5, IGF Binding Protein 7, HLA-A0202 heavy chain, Activin A (βA subunit), TNF RII, SPC4, and CNTF Rα, in cells obtained from a subject suspected of having, or at risk of having malignant melanoma. The levels of such melanoma skin marker products are indicative of malignant melanoma when compared to a normal or standard polypeptide profiles in a similar tissue. Thus, the expression pattern of a melanoma skin marker product will vary depending upon the presence and stage of malignant melanoma.

In this regard, the sample, as described herein, can be used as a source to isolate polypeptides. Measurement of a particular polypeptide, for example IL-1 RI, endothelin-2, ephrin-A5, IGF Binding Protein 7, HLA-A0202 heavy chain, Activin A (βA subunit), TNF RII, SPC4, and CNTF Rα, can serve as a method of detecting, staging, diagnosing, monitoring, prognosing, or otherwise assisting in management of malignant melanoma. For example, following skin scraping or skin stripping, using the methods described above, cells isolated from the stratum corneum may be lysed by any number of means, and polypeptides obtained from the cells. These polypeptides may then be quantified using methods known to those of skill in the art, for example by ELISA.

Monoclonal antibodies to a particular polypeptide, for example, example IL-1 RI, endothelin-2, ephrin-A5, IGF Binding Protein 7, HLA-A0202 heavy chain, Activin A (βA subunit), TNF RII, SPC4, and CNTF Rα, can be used in immunoassays, such as in liquid phase or bound to a solid phase carrier, to detect polypeptide associated with a disorder, such as dermatitis. In addition, the monoclonal antibodies in these immunoassays can be detectably labeled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the polypeptide antigens using the monoclonal antibodies of the invention can be done utilizing immunoassays, which are run in either the forward, reverse, or simultaneous modes, including immunohistochemical assays on physiological samples. Those of skill in the art will know, or can readily discern, other immunoassay formats without undue experimentation. In addition, there are a number of commercially available antibodies to cytokines of interest.

The term "immunometric assay" or "sandwich immunoassay" includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of a cytokine polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation. A cytokine polypeptide may be detected by the monoclonal antibodies when present in biological fluids and tissues such as a skin sample.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-cytokine immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1-100 µg/µl) may be important, in order to maintain the proper sensitivity yet inhibit any unwanted interference by mutually occurring cross reactive proteins in the specimen.

"Cytokine" as used herein means any number of factors that play a role in cellular regulation or differentiation. For example, cytokines can include the family of interleukins (IL) including IL-1, IL-2, IL-3, IL-4, IL-5, IL-6, IL-8, IL-9, IL-13, IL-14 as well as factors belonging to the transforming growth factor beta (TGF-β) superfamily, GM-CSF and interferon.

As used herein, the term "biological factor" means a number of factors that have biological activity or play a biological role. For example, biological factor includes polynucleotides, such as DNA, RNA, mRNA and cDNA, polypeptides, such as IL-4, IL-8, and IL-13 proteins and fragments thereof, as well as lipids such as cholesterol, fatty acids, and inflammatory mediators such as leukotrienes, prostaglandins and others.

In another aspect, the present invention provides a non-invasive method for monitoring a suspicious lesion of a subject. The method includes analyzing expression of one or more melanoma skin markers in a skin sample taken from the suspicious lesion at a first time point and a second time point, and comparing the expression at the first time point and the second time point. The melanoma skin markers include IL-1 RI, endothelin-2, ephrin-A5, IGF Binding Protein 7, HLA-A0202 heavy chain, Activin A (βA subunit), TNF RII, SPC4, and CNTF Rα. Expression of the melanoma skin markers is related to melanoma, such that a change in the expression of one or more of the melanoma skin markers over time is indicative of melanoma. In certain preferred embodiments, the skin sample includes nucleic acids, and is a human skin sample.

Time points can include any interval of time, but are typically at least 2 weeks, and more typically at least 1 month apart. For certain embodiments, time points are 2 months, 3 months, 6 months, 1 year, or 2 years apart. Samples can be taken at any number of time points, including 2, 3, 4, 5, etc. time points. Comparison of expression analysis data from different time points can be performed using any of the known statistical methods for comparing data points to assess differences in the data, including time-based statistical methods such as control charting. Melanoma can be identified in the time series, for example, by comparing expression levels to a cut-off value, or by comparing changes in expression levels to determine whether they exceed a cut-off change value, such as a percent change cut-off value.

In another aspect, the present invention provides a non-invasive method for detecting expression of IL-1 RI, endothelin-2, ephrin-A5, IGF Binding Protein 7, HLA-A0202 heavy chain, Activin A (βA subunit), TNF RII, SPC4, and CNTF Rα in a skin sample. The method includes obtaining a skin sample by applying an adhesive surface to the skin and removing the adhesive surface from the skin such that a skin sample comprising nucleic acid in an amount sufficient for subsequent detection adheres to the adhesive surface after its removal. Then, analyzing expression of IL-1 RI, endothelin-2, ephrin-A5, IGF Binding Protein 7, HLA-A0202 heavy chain, Activin A (βA subunit), TNF RII, SPC4, and CNTF Rα in the nucleic acids of the skin sample. As disclosed herein, this method is useful for detecting, diagnosing, staging, monitoring, and managing malignant melanoma.

In another embodiment the invention provides a kit for detecting malignant melanoma. The kit includes one or more detection reagents, for example oligonucleotide primers or probes that are complementary to a polynucleotide sequence encoding at least one of IL-1 RI, endothelin-2, ephrin-A5, IGF Binding Protein 7, HLA-A0202 heavy chain, Activin A (βA subunit), TNF RII, SPC4, and CNTF Rα. The oligonucleotide primers can be spotted on a bioarray which is provided in the kit. The kit can include a skin sample collection device and probes that selectively bind to IL-1 RI, endothelin-2, and ephrin-A5. Such a kit may also include a carrier means being compartmentalized to receive in close confinement one or more containers such as vials, tubes, and the like, each of the containers comprising one of the separate elements to be used in the method. If present, a second container may comprise a lysis buffer. The kit can alternatively include a computer-type chip on which the lysis of the cell will be achieved by means of an electric current.

The kit, in preferred embodiments, includes a skin sample collection device such as a rigid instrument capable of removing the epidermal layer of the skin (e.g. a sterile #15 scalpel), and/or an adhesive surface, such as an adhesive tape, for example, Duct tape (333 Duct tape, Nashua tape products), Scotch® tape (3M Scotch 810, St. Paul, Minn.), or a similar product. A preferred adhesive tape is D-SQUAME® (CuDerm, Dallas, Tex.). The kit can also include a cell lysis buffer suitable for preserving nucleic acids in the skin sample.

The kit can also have containers containing probes or primers for amplification of or hybridization to the target nucleic acid sequence which may or may not be labeled, or a container comprising a reporter, such as a biotin-binding protein, such as avidin or streptavidin, bound to a reporter molecule, such as an enzymatic, florescent, or radionuclide label. The term "detectably labeled deoxyribonucleotide" refers to a deoxyribonucleotides that is associated with a detectable label for detecting the deoxyribonucleotide. For example, the detectable label may be a radiolabeled nucleotide or a small molecule covalently bound to the nucleotide where the small molecule is recognized by a well-characterized large molecule. Examples of these small molecules are biotin, which is bound by avidin, and thyroxin, which is bound by anti-thyroxin antibody. Other methods of labeling are known to those of ordinary skill in the art, including enzymatic, fluorescent compounds, chemiluminescent compounds, phosphorescent compounds, and bioluminescent compounds.

The kit can include one or more primer pairs, including a forward primer that selectively binds upstream of a melanoma skin marker gene on one strand, and a reverse primer, that selectively binds upstream of a melanoma skin marker gene on a complementary strand. The melanoma skin marker genes are typically one or more of Interleukin-1 RI (IL-1 RI), endothelin-2, ephrin-A5, Insulin-like Growth Factor (IGF) Binding Protein 7, Human Leukocyte Antigen (HLA)-A0202 heavy chain, Activin A (βA subunit), Tumor Necrosis Factor (TNF) RII, SPC4, and Ciliary Neurotrophic Factor (CNTF) Rα. Primer pairs according to this aspect of the invention are typically useful for amplifying a polynucleotide that corresponds to a melanoma skin marker genes using amplification methods described herein.

In another aspect the invention provides a method of screening for compounds or identifying compounds which may cause or prevent malignant melanoma, or which may be used to treat malignant melanoma. In this aspect, for example, cells of the skin, such as epidermal cells, including keratinocytes and melanocytes, or dermal cells, such as fibroblasts, are contacted with a test compound under conditions which would induce malignant melanoma formation. The expression of melanoma skin markers is then detected.

The conditions under which contact is made are variable and will depend upon the type of compound, the type and amount of cells in the skin to be tested, the concentration of the compound in the sample to be tested, as well as the time of exposure to the compound. The skill in the art in determining the proper conditions under which a compound may cause melanoma are known and would require only routine experimentation, if any. The skin cells may be isolated using the techniques described above, e.g. by scraping or tape stripping, the cells may then be exposed to the test compound in vitro. Alternatively, cultured skin cells or skin constructs may be used. For example, skin cells may be cultured from any source under standard cell culture conditions on a solid or semi-solid support until they become sufficiently confluent. Upon confluence or subconfluence the cells are then exposed to the test compound. Polynucleotides are then isolated from the cells which have been exposed to the compound and quantitated as described above.

For example, and not by way of limitation, skin cells can be isolated by the tape or scraping method above and mRNA isolated. The mRNA can then be quantified using the probes for particular melanoma skin markers. Alternatively, the mRNA may be amplified by RT-PCR prior to detection of the polynucleotide. As described above, quantitation of a polynucleotide derived from a melanoma skin marker, can be used to detect, diagnose, stage, screen, and assist in management, of malignant melanoma.

The present invention is not to be limited in scope by the specific examples provided for below, which are intended as single illustrations of individual aspects of the invention and functionally equivalent methods and components are within the scope of the invention.

EXAMPLE 1

Non-Invasive Recovery of Sub-Stratum Corneum Cells

A. Recovery Using a Rigid Surface

Skin cells can be recovered non-invasively by scraping the skin with a sterile #15 scalpel. The scalpel is held at an angle approximately 15 degrees from horizontal and repeatedly but gently scraped across an area of skin that is approximately 1×1 cm in size. The epidermal cells are transferred to a sterile tissue culture well by scraping the blade against the interior wall of the well. When the glistening epidermal layer is reached, the scraping is stopped prior to causing any bleeding, to avoid contaminating the scraping(s) with blood. The cells are deposited in a sterile 1 cm petri dish and about 300 ml of lysis buffer is added to the culture well. The lysis buffer is pipetted up and down until the epidermal cells are completely lysed.

RNA lysis buffer is added within 10 minutes of initiation of the scraping. The sterile tissue culture well is maintained on dry ice. The cells are dissolved in the RNA lysis buffer, transferred into RNAse free centrifuge tubes and the total RNA is extracted.

B. Recovery Using an Adhesive Surface

Skin cells can be recovered non-invasively by using Duct tape (333 Duct tape, Nashua tape products), Scotch® tape (3M Scotch® 8 10, St. Paul, Minn.), D-SQUAME® (CuDerm, Dallas, Tex.), or a similar product. The skin is stripped up to a maximum 25 times. Additionally, it will be recognized that the stickier the tape, the fewer strippings are required. The skin cells were recovered by vortexing and then centrifuging the tape in an RNAse-free Eppendorf tube containing lysis buffer. The same lysis buffer was reused for each piece of tape used at a single skin site. The entire procedure was performed in less than 90 minutes. The process of tape stripping itself does not affect the skin cytokine profile during the first few hours after the procedure is done. Moreover, during the early hours after stripping no inflammatory cells migrate from the circulation into the dermis or epidermis.

RNA was immediately extracted from cells adhering to the strip by vigorously vortexing the tape in 0.5 ml TriReagent (Molecular Research Center, Inc., Cincinnati, Ohio). Yeast transfer RNA (4 µg) was then added as carrier RNA before the total RNA was isolated and purified according to the manufacturer's instructions. The total isolated RNA from each sample was used in an RNAse protection assay (RiboQuant® Multiprobe RNAse Protection Assay System, PharMingen, Inc., San Diego, Calif.) without prior measurement of the amount of RNA by OD measurement. Assays were performed with samples on standard acrylamide sequencing gels and used to identify digested cytokine messages. Gels containing digested RNA bands were first exposed to a Phosphor Screen (Molecular Dynamics, Inc., Sunnyvale, Calif.). The exposed screen was then scanned with a phosphorimager Storm 860 (Molecular Dynamics, Inc.). Intensities of bands in each sample were analyzed with the software ImageQuant™ (Molecular Dynamics, Inc.).

Appropriate care should be taken to prevent RNAse contamination of the samples since skin is a rich source of RNAse that can quickly degrade RNA released from damaged epidermal cells. The sample collection and extraction techniques described herein demonstrate that skin RNA can indeed be obtained without significant degradation as indicated by the ability to detect mRNA by RPA.

EXAMPLE 2

Analysis Of Cells Obtained By Tape Stripping

Irritant contact dermatitis (ICD) was induced by applying 0.5% sodium lauryl sulfate (SLS) in distilled water for 72 hours to the upper arm. After this exposure, the erythema was graded according to standard scoring sales (Fisher's Contact Dermatitis. 4th ed. Rietschel, R. L. and Fowler, J. F. Jr. eds. Williams & Wilkins, Baltimore, 1995, pg. 29). Allergic contact dermatitis (ACD) was induced by applying dibutyl squarate in acetone to the upper arm of the same subject under occlusion for 48 hours. The upper arms of the same individual (subject #1) were tape stripped 12 times and processed as described in Example 2 above.

FIG. 1, lane 1 shows the RNA isolated from an ACD erythematous area of skin, read clinically as 3+erythema, that was induced by squarate. Lane 3 is the RNA from ICD erythematous skin, clinically scored as 2+erythema, induced after exposure to 0.5% SLS. After exposure of the x-ray film, the band for cytokine IL-4 can be clearly seen in lane 1, but not in lane 3 which contains RNA from ICD cells. Thus, the cytokine pattern in the ACD reaction clearly differed from the ICD reaction and normal skin seen in lane 2.

Figure 2:
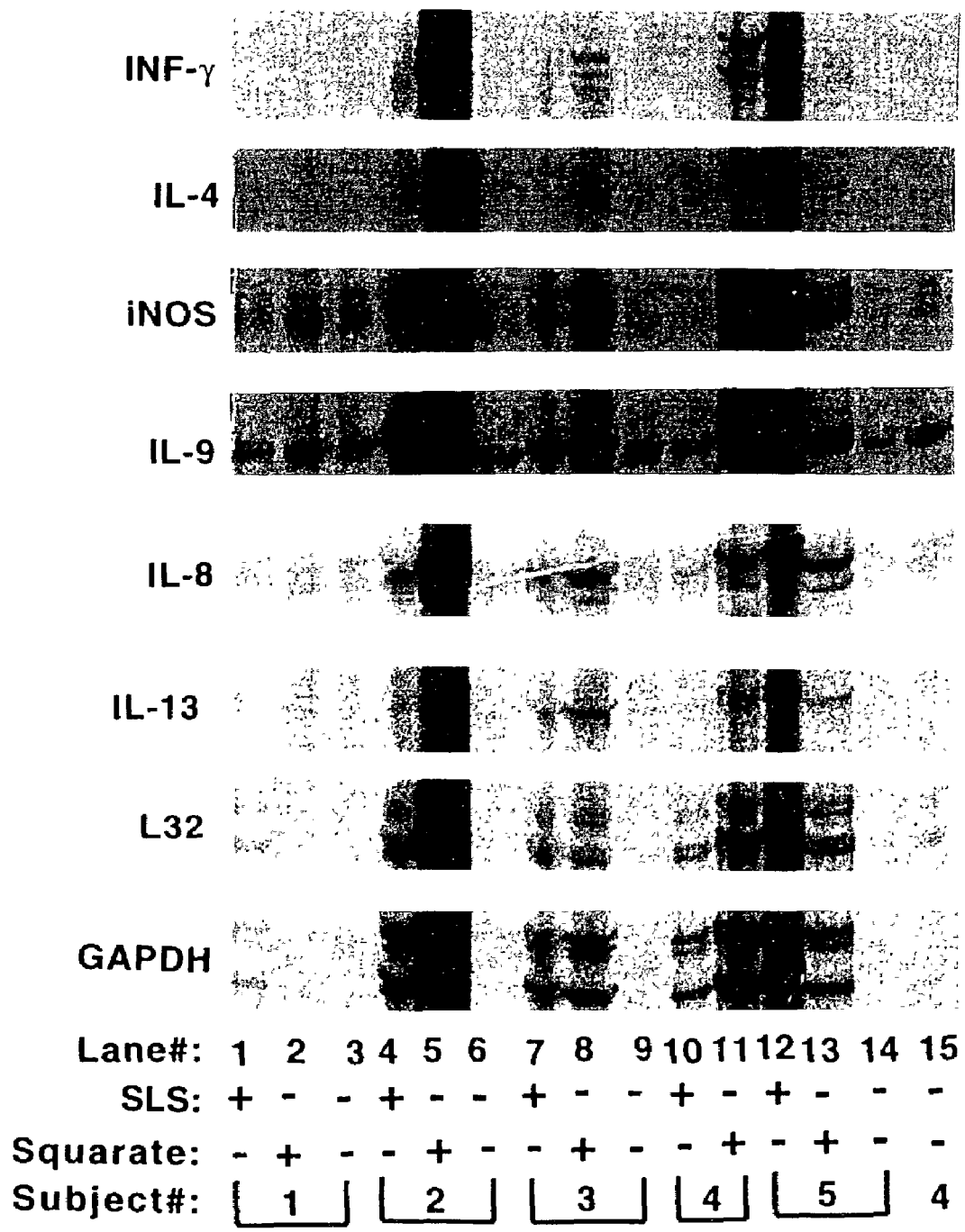
FIG. 2 shows results for RPA performed with RNA obtained by tape stripping three different areas of the upper arm of four more individuals. Riboprobes for 6 different RNAs (IL-4, IL-8, IL-9, IL-13, IL-14 and an isoform of nitric oxide synthase (iNOS)) plus 2 housekeeping genes were included in this gel. The "+" indicates that the skin harvested from the subject had been treated either with SLS (second row at bottom of figure) or squarate (third row at bottom of figure).

In a subsequent experiment, all subjects with dermatitis had mRNA encoding the cytokine IL-4 in cells from skin in areas that had demonstrated an ACD reaction (lanes 8, 11, 13 in FIG. 2). By contrast, IL-4 was not visible in any of the ICD treated areas of skin or in normal skin samples obtained from the same subjects. Furthermore, in 4 of 5 subjects (subjects 2, 3, 4 and 5 in FIG. 2), IL-8 was present in erythematous areas of skin, whether the erythema was induced by an irritant or an allergic reaction, but not in the RNA obtained from normal skin. Thus, IL-8 mRNA was generically indicative of dermatitis.

The mRNA encoding IL-13, a cytokine secreted by activated T cells, was present in 3 of the 4 erythematous areas of skin (lanes 5, 8, 11, 13 in FIG. 2) in which allergic inflammation had been induced by squarate. A faint band could be seen in the approximate area(s) expected to contain the mRNA with the molecular weight associated with gamma interferon (IFN-γ) (lanes 8 and 11 in FIG. 2). These bands were present in the mRNA extracted from 2 of the 5 squarate (ACD) treated skin samples. As was the case for IL-13, the tentative band for IFN-γ mRNA was seen in the same lanes that also had mRNA for IL-4.

IL-14, a B cell growth factor, was present in some of the squarate treated skin samples as well as some of the SLS treated skin samples (FIG. 2). IL-9, a multifunctional cytokine, was detected in all 13 samples that could be visualized in this experiment. In addition, the mRNA for the inducible isoform of nitric oxide synthase (iNOS) and IL-9 were seen in every lane that could be visualized clearly (13 of 15 samples) (FIG. 2). The presence of IL-4 in the same lanes as IL-13 strongly suggests that these two cytokine markers were induced by an allergic reaction in the skin from which the samples were obtained.

The clinical quantification of the erythema visualized in the various skin reactions is documented in Tables 1 and 2.

TABLE 1

ACD REACTIONS

| SUBJECT | SKIN REACTION | IL-4 | IL-8 | IL-9 | IL-13 | iNOS | IFNγ |
|---------|---------------|------|------|------|-------|------|------|
| #1 | 0 | ND | ND | + | ND | + | ND |
| #2 | 2+ | + | + | NT | NT | NT | NT |
| #3 | 2+ | + | + | + | + | + | + |
| #4 | 2+ | + | + | * | + | * | + |
| #5 | 2+ | + | + | + | + | + | + |

ND = not detected
2+ = moderate erythema (red)
* gel not readable
NT = not tested

TABLE 2

ICD REACTIONS

| SUBJECT | SKIN REACTION | IL-4 | IL-8 | IL-9 | IL-13 | iNOS | IFNγ |
|---------|---------------|------|------|------|-------|------|------|
| #1 | 0 | ND | ND | + | ND | + | ND |
| #2 | 2+ | + | + | NT | NT | NT | NT |
| #3 | 1+ | ND | + | + | + | + | ND |
| #4 | 1+ (low) | ND | ND | + | ND | ND | ND |
| #5 | 3+ | * | + | * | * | * | * |

ND = not detected
* gel not readable
NT = not tested
1+ = mild erythema (pinkish)
2+ = moderate erythema (red)
3+ = strong erythema (beet red)

EXAMPLE 3

To further examine the relationship between the cytokines and the degree of inflammation in subject numbers 3-5, the IL-4, IL-8 and IL-13 RNA levels were normalized to the corresponding housekeeping gene levels (Table 3). Among the three subjects analyzed, a correlation exists between the RNA levels and the severity of the reactions. Table 2 shows that the samples from the strongest skin reactions were also the ones that demonstrated the largest relative amount of IL-8 in the ACD reaction. For example, subject #4 with a 2+reaction at the ACD site and only a slight (low+1) reaction at the ICD site showed an approximate two fold difference in the IL-8/GAPDH ratios when comparing the ICD and ACD reactions using the RPA method described above. In addition, one would predict an ACD reaction if, on the gel, there is a band for IL-4 and a value for IL-4/GAPDH of about 0.001 or higher. Also, an ACD reaction can be confirmed where there is an IL-13 band with an IL-13/GAPDH value of about 0.13 or higher (Table 3).

TABLE 3

| Subject | TYPE OF REACTION | ICD | ACD |
|---------|------------------|------|------|
| 3 | IL-4/GAPDH | NC | NC |
|   | IL-8/GAPDH | 0.3495 | 0.8867 |
|   | iNOS/GAPDH | 0.2202 | 0.2652 |
|   | IL-13/GAPDH | 0.070 | 0.251 |
| 4 | IL-4/GAPDH | 0 | 0.01559 |
|   | IL-8/GAPDH | 0.2879 | 0.61080 |
|   | iNOS/GAPDH | 0.07107 | 0.2661 |
|   | IL-13/GAPDH | 0.117 | 0.134 |
| 5 | IL-4/GAPDH | 0 | 0.07255 |
|   | IL-8/GAPDH | 0.2541 | 1.3023 |
|   | iNOS/GAPDH | 0.05315 | 0.1951 |
|   | IL-13/GAPDH | 0.055 | 0.158 |

NC = not calculated

A number of embodiments of the present invention have been described. Nevertheless, it will be understood that various modifications may be made without departing from the spirit and scope of the invention. Accordingly, other embodiments are within the scope of the following claims.

EXAMPLE 4

This example identifies genes which are differentially expressed at the mRNA level, in early or late stage melanoma cells compared to normal cells. These genes are melanoma skin markers according to the present invention. An adhesive tape was used to obtain mRNA from frozen tissue samples of malignant melanoma and control nevi, and skin surface gene expression profiling studies (SSGEP) with a cDNA array were performed, to produce a set of potential genetic markers that can be utilized for a non-invasive molecular diagnostic screening procedure for melanoma. Candidate genes that were identified on the cDNA array were further investigated using RT-PCR with SYB-R green detection. The genes encoding IL-1 RI, endothelin-2, and ephrin-A5 were found to be differentially regulated between control nevi and early melanoma using the SSGEP procedure on frozen tissue samples. Likewise, the genes encoding IGF Binding Protein 7, HLA-A0202 heavy chain, Activin A (βA subunit), TNF RII, SPC4, and CNTF Rα were found to be differentially regulated between control nevi and advanced melanoma. Identification of genes implicated in the progression of early stage melanoma is important for developing molecular diagnostic assays for screening and staging melanoma, as well as for developing more effective therapeutics for this deadly disease.

Since melanoma appears to modulate gene expression of neighboring cells, it was hypothesized that it may be possible to detect early melanoma by examining gene expression profiles of outer skin cells overlying a suspicious lesion. Neighboring effects are most obvious and well documented for various secreted cytokines. For example, it has been previously described for the expression of macrophage migratory inhibitory factor, MIF, that it stimulates the expression of metalloproteinases in fibroblasts, which may help to invade the dermis in case of a malignant tumor that excessively produces MIF (Onodera S, et al., *J. Biol. Chem.* 275:444-450, 2000). MIF was found by our coworkers to be overexpressed in highly tumorigenic variants of melanoma cell lines if compared to less tumorigenic variants (Vogt et al., *Submitted,* 2001). Similar neighboring effects may happen in the keratinocyte population, too: In the case of melanoma detection, basal cells that were formerly in the vicinity of a melanocyte, and have migrated into the upper epidermis through the differentiation process, may preserve mRNA profiles induced in response to the underlying melanoma, and paracrine effects of a plethora of pathological cytokines may induce a characteristic profile of the keratinocytes adjacent to the tumor and higher upwards in the epidermis. This is reflected by the clinical finding, that advanced tumors often lead to atrophy and erosion of the epidermis overlaying the lesion.

Molecular analysis of cells in their native environment is thought to provide the most accurate picture of the in vivo disease state (Liotta and Petricoin, *Nature Reviews/Genetics* 1:48-56, 2000). Since biopsied tissues are three dimensional structures containing numerous interacting cellular subpopulations, it is difficult to isolate the molecular signatures of a particular cell type. The present Example utilizes a method for obtaining a sample from the surface of a suspected melanoma lesion or a control nevi.

In order to develop a non-invasive molecular diagnostic assay for early melanoma detection, the use of a skin surface sampling method was combined with a specialized cDNA array to determine differentially expressed genes between malignant melanoma and normal nevi. The gene array contained approximately 600 genes, specific for cytokines, receptors, and growth factors. An adhesive tape was utilized to obtain skin cells. This technique is referred to herein as skin surface gene expression profiling (SSGEP).

In SSGEP, epidermal cells are removed using a tape stripping methodology in which successive tapes are applied to the same skin site, and removed in a rapid progression, until a sufficient depth is reached for sampling gene expression profiles (need tape stripping reference). The epidermis consists predominantly of keratinocytes (>90%), which differentiate from the basal layer, moving outward through various layers having decreasing levels of cellular organization, to become the cornified cells of the stratum corneum layer. Renewal of the epidermis occurs every 20-30 days in normal skin. Other cell types present in the epidermis include melanocytes, Langerhans cells, and Merkel cells.

Since melanoma appears to modulate gene expression of neighboring cells, it was hypothesized that it may be possible to detect early melanoma by examining gene expression profiles of outer skin cells overlying a suspicious lesion. Neighboring effects are most obvious and well documented for various secreted cytokines. For example, it has been previously described for the expression of macrophage migratory inhibitory factor, MIF, that it stimulates the expression of metalloproteinases in fibroblasts, which may help to invade the dermis in case of a malignant tumor that excessively produces MIF (Onodera et al., *J. Biol. Chem.* 275:444-450, 2000). MIF was found by our coworkers to be overexpressed in highly tumorigenic variants of melanoma cell lines if compared to less tumorigenic variants (Vogt et al., *Submitted*, 2001). Similar neighboring effects may happen in the keratinocyte population, too. In the case of melanoma detection, basal cells that were formerly in the vicinity of a melanocyte, and have migrated into the upper epidermis through the differentiation process, may preserve mRNA profiles induced in response to the underlying melanoma, and paracrine effects of a plethora of pathological cytokines may induce a characteristic profile of the keratinocytes adjacent to the tumor and higher upwards in the epidermis. This is reflected by the clinical finding, that advanced tumors often lead to atrophy and erosion of the epidermis overlaying the lesion.

Materials and Methods

Tape Stripping

Frozen tissue samples for gene expression profiling studies of malignant melanoma were obtained from the University of Regensburg Department of Dermatology. A group of six control benign nevi, four early malignant melanoma samples (Pagetoid epidermal scattering), and 4 advanced malignant melanoma samples (epidermal atrophy) were randomly selected from the tissue collection. D-squame tapes (Cu-Derm, Tex.) were utilized to isolate skin cells from the frozen biopsies for skin surface gene expression profiling. The D-squames were cleaned with RNA zap (Ambion) prior to use. The surface of the biopsy samples was cleaned with alcohol, dried, and then moistened with a $\frac{1}{10}$ dilution of commercial RNAse inhibitor. Isolation of skin cells from the frozen biopsy samples was performed in a cryostat by pressing a D-squame tape tightly against the tissue, quickly removing the tape, and repeating this tape-stripping procedure until the tape surface was covered with cells. Up to 30 tapes were collected in this manner from a single biopsy, and placed in a sterile RNase free culture dish. The D-Squame tape samples were stored at $-80°$ C. until the next processing step.

RNA Extraction

D-squame tape samples were brought to $-20$ in the cryostat. For RNA extraction, tapes from a single biopsy sample were successively submersed in one volume (750 µl) of RLT lysis buffer (Qiagen) in a microcentrifuge tube by placing the tapes individually in the microcentrifuge tube containing the RLT buffer, performing a rapid freeze-thaw cycle in liquid nitrogen, and scraping the tape surface with a sterile inoculation loop. After extraction, each tape was removed using forceps and discarded. The procedure was repeated until all tapes in the pool were extracted. RNA was isolated following the RNeasy protocol, with on column DNAase digest. RNA was eluted from the column using 30 µl of RNAse free water (Promega), and concentrated to about 5 µl at 4° C. using a Speed Vic.

Synthesis of cDNA

Double-stranded cDNA was synthesized by reverse transcription of the total RNA and subsequent amplification of the first strand cDNA using the SMART PCR II kit (Clontech). The optimum number of PCR cycles was determined by taking aliquots from the PCR reaction after 10, 15, 20, and 25 reaction cycles, and analyzing by gel electrophoresis. The lane on the gel having a moderately strong smear of cDNA ranging from 0.5 to 6 kb, and several bright bands, was chosen to represent the optimum number of PCR cycles for an abundance of cDNA transcripts. A second reaction was prepared and cycled to this optimal number of cycles. The Qiagen PCR purification kit was utilized to purify the double stranded cDNA (Becker et al., *J. Invest. Dermatol.* 116:983-988, 2001).

Probe Labeling

Approximately 25 ng of the double stranded cDNA from the PCR reaction was labeled with α $^{32}$P-deoxycytidine triphosphate using randomly primed Klenow fragment synthesis. Non-incorporated nucleotides were removed using the Nuctrap and beta shield kits (Stratagene).

Array Hybridization

The Sigma Panorama array, containing 600 cytokines, receptors, and growth factors was used to probe for differentially expressed genes in the malignant melanoma biopsies (Sigma-Genosys, The Woodlands, Tex.). The Sigma Panorama filter array was prehybridized for 24 hours in 5 mL of Sigma-Genosys hybridization solution at 65 C. The $^{32}$P-labeled cDNA samples (probes) were denatured for 2 minutes in a boiling water bath, and then applied to the filter array for 48 hours at 65 C. The filter array was washed three times with a 0.5×SSPE/1% SDS solution (RT solution I) for 3 minutes, and once with RT Solution II at 65 C for 20 minutes (0.1×SSPE/1%SDS). The array filter was exposed to autoradiography film for 24-48 hours and to phosphor imager cassettes for quantitation.

Quantitation of Hybridization Signals

The hybridization signals were measured by a phosphor imager, and analyzed using the AIDA Metrix$^R$ software (Raytest). A background correction was performed, and the signals were normalized using the signals from the housekeeping genes. For each group of malignant melanoma samples (early and late stage), pair-wise comparisons were made between the malignant melanoma samples and the normal nevi control samples based on the normalized integrated signal intensities. Signals for candidate genes differing by more than a factor of three were identified, and statistical significance was determined using a non-parametric test (U test).

RT-PCR Confirmation of Markers

Real time RT-PCR with SyBr Green detection was utilized to verify IL1-RI results in a semi-quantitative manner, the relative abundance of the candidate marker genes with respect to the control gene GAPDH. For example, for IL1 RI expression analysis using RT-PCR, the primers of SEQ ID NO:1 and SEQ ID NO:3 were used.

Results

By comparing skin surface gene expression profiles in early malignant melanoma with control nevi, three differentially expressed genes were identified (Table 4). For advanced malignant melanoma, six differentially expressed genes were identified by comparison with the control nevi (Table 5). Each gene identified in a malignant melanoma group (early or advanced) was differentially expressed in all four of the melanoma samples. The differentially expressed genes in the early malignant melanoma group were distinct from those in the advanced group.

TABLE 4

Markers discriminating early melanomas from nevi.

| Endothelin-2 | p = 0.005 |
|---|---|
| ephrin-A5 | p = 0.009 |
| IL-1 RI | p = 0.009 |

TABLE 5

Markers discriminating advanced melanomas from nevi.

| HLA-A 0201 heavy chain | p = 0.002 |
|---|---|
| Activin A (bA subunit) | p = 0.002 |
| IGF Binding Protein 7 | p = 0.003 |
| TNF RII | p = 0.03 |
| SPC4 | p = 0.03 |
| CNTF Ra | p = 0.03 |

Figure 3:
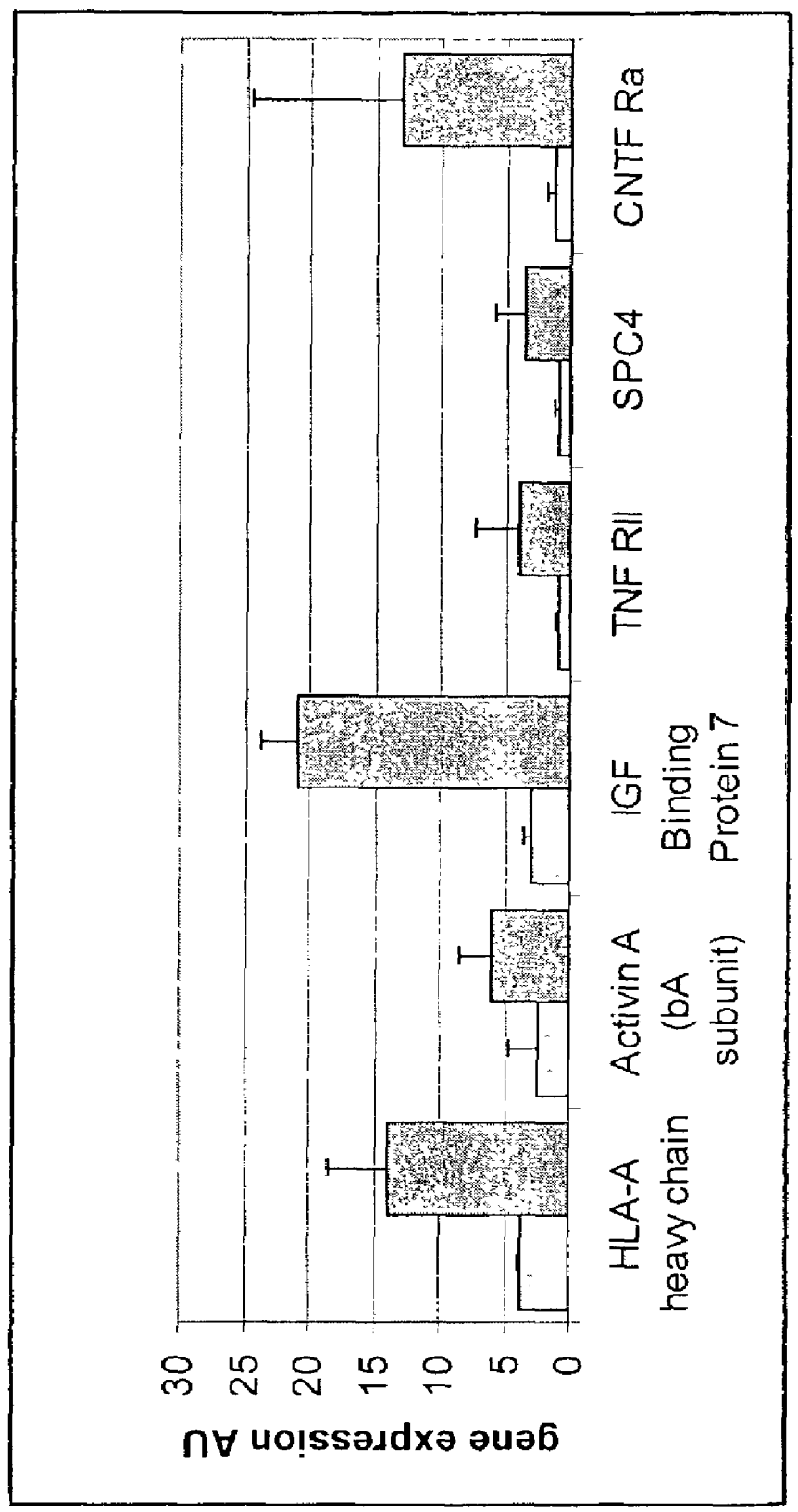
FIG. 3 shows quantitative analysis of expression of melanoma skin markers (as indicated under bars) in nevi versus advanced malignant melanoma samples. Dark bars are expression in adhesive tape from advanced malignant melanoma. Light bars are expression in adhesive tape from melanocytes nevi (benign controls). Gene expression arbitrary units are based on phosphor imaging of array.

Expression levels for all of the advanced stage melanoma skin markers identified herein, in benign nevi versus advanced malignant melanoma are shown in FIG. 3. The expression levels of all of the advanced stage melanoma skin markers were higher in advanced malignant melanoma samples than in benign nevi.

Figure 4:
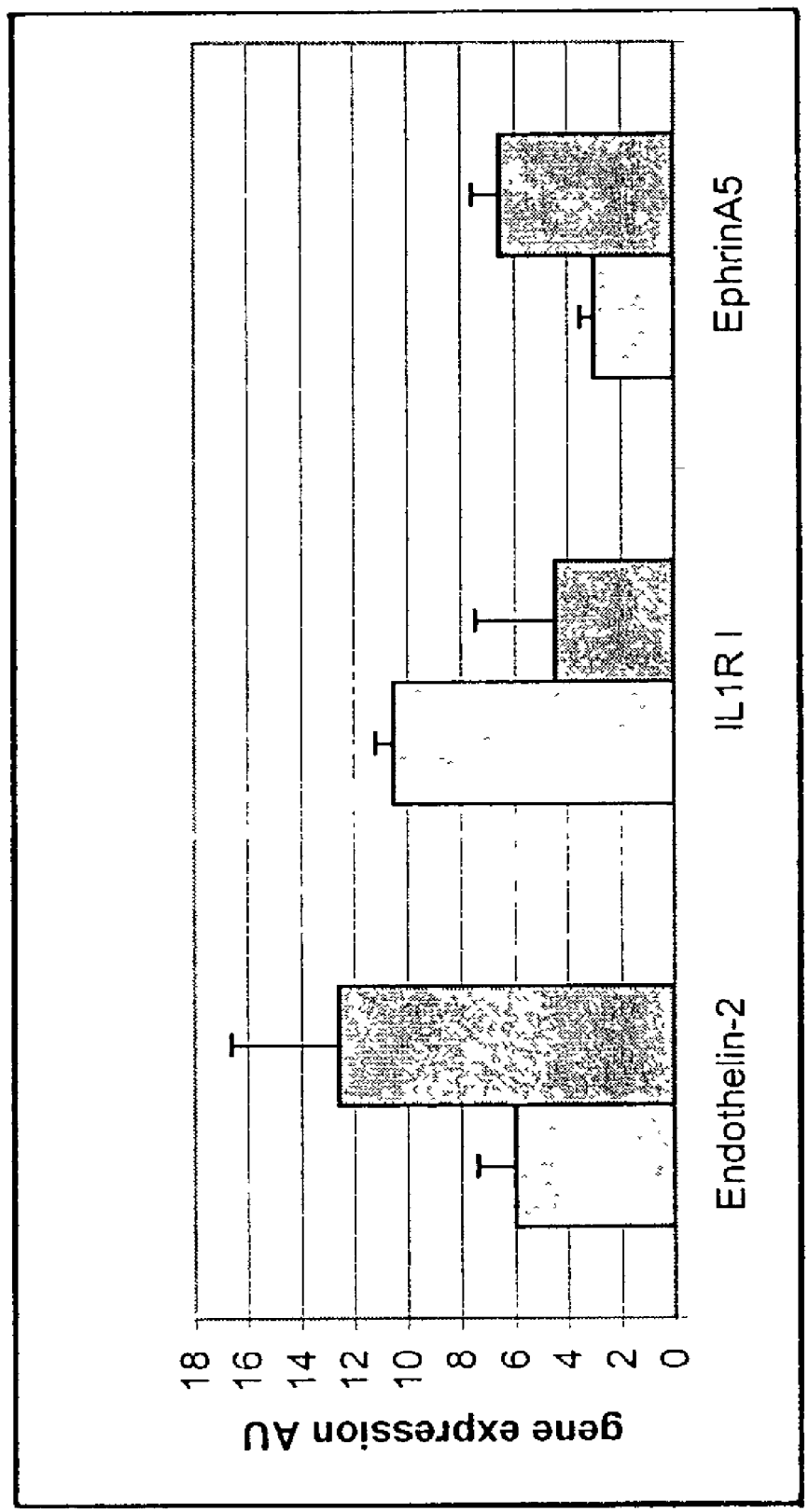
FIG. 4 shows quantitative analysis of expression of melanoma skin markers (as indicated under bars) in nevi versus early malignant melanoma samples. Dark bars are expression in adhesive tape from early malignant melanoma. Light bars are expression in adhesive tape from melanocytes nevi (benign controls). Gene expression arbitrary units are based on phosphor imaging of array.

Expression levels for all of the early stage melanoma skin markers identified herein, in benign nevi versus advanced malignant melanoma are shown in FIG. 4. The expression levels of all of endothelin-2 and ephrinA5 were higher in early stage malignant melanoma samples than in benign nevi. The expression level of IL1 RI was lower in early stage melanoma than in benign nevi.

Figure 5:
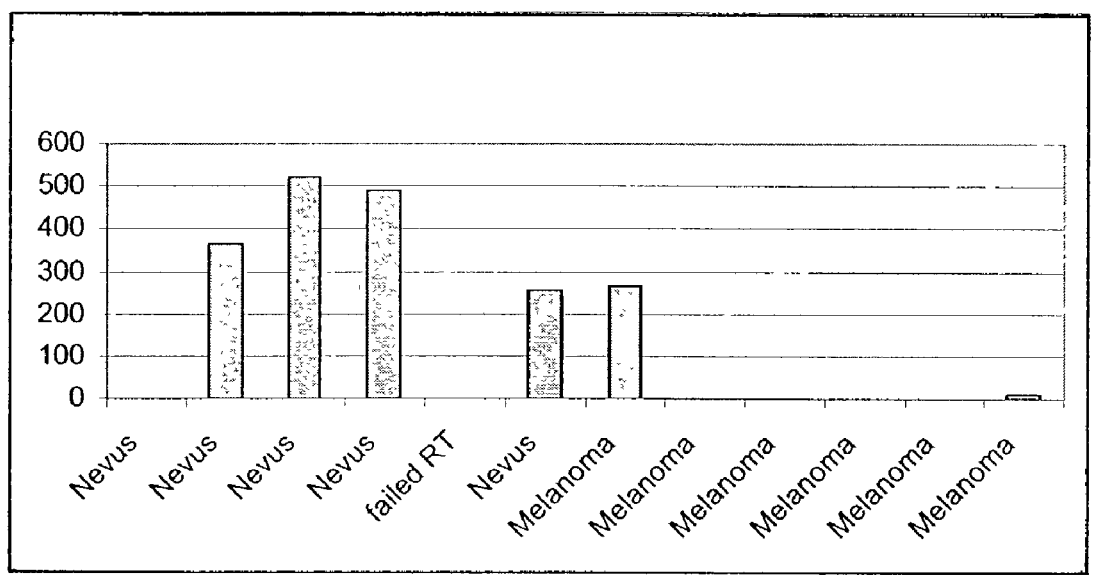
FIG. 5 shows semi quantitative real time PCR results for expression of the IL1 RI gene in nevus versus melanoma samples. Quantitation was based on SyBr green incorporation values, normalized by GAPDH expression.

Semi-quantitative RT PCR of IL1 RI gene expression, was performed on a set of tape sampled material different from that used for the experiment described above. Among 11 patient tape samples, IL1 RI gene expression was lower in melanoma samples than in benign samples, except for one false negative (i.e. malignant melanoma patient sample with an elevated IL1 RI reading), and one false positive reading (i.e. benign nevi patient sample with a depressed IL1 RI reading) (FIG. 5).

Discussion

Over 100 genes have been reported to have significance in the progression of malignant melanoma (see Table 6). A few potentially promising candidates under discussion, P16, CDKN2A, melastatin, and the Mage-A family of genes are among those reported to have potential diagnostic or prognostic value.

While germline mutations in p16 or CDKN2A are found in a significant percentage of relatively rare melanoma families, p16 mutations are rare in sporadic tumors (Bataille, *Clin. Exp. Dermatol.* 25(6):464-467, 2000). Deletion or inactivation of CDKN2A appears to be involved in the progression rather than the initiation of sporadic malignant melanoma (Cachia et al., *Clin. Cancer Res.*6(9):3511-3515, 2000).

Based on in-situ hybridization studies with biopsy samples, it was recently reported that melastatin mRNA expression appeared to correlate with melanocytic tumor progression, melanoma tumor thickness, and the potential for melanoma metastasis (Deeds et al., *Human Pathology* 31(11):1346-1356, 2000; Duncan et al., *Journal of Clinical Oncology* 19(2):568-576, 2001). The loss of melastatin mRNA expression correlated with poor prognosis. Down-regulation of the melastatin gene was originally observed using a mouse melanoma cell line, B16, with high metastatic potential (Duncan et al., *J Clin Oncol,* 19(2):568-76, 2001). Since the melastatin marker appears to be melanocyte specific, a prognostic assay based on melastin mRNA will most likely require a biopsy.

A genetic test based on three members of a family of cancer related genes called MAGE-A was recently reported for the detection of metastatic cancer in blood or tissue (Miyashiro et al., *Clinical Chemistry* 47(3):505-512, 2001). A multiplex assay is advantageous, since gene markers are often expressed at a low frequency, and variations in gene expression profiles exist across individuals. While 40% of the patients with stage IV melanoma had detectable levels of Mage-A mRNAs in their blood samples, 0% of stage I patients, and 14% of stage II or stage III patients exhibited detectable Mage-A mRNAs.

Using a hierarchical clustering algorithm, it was recently shown that differentially regulated genes in melanoma biopsy samples were, related to a vascular-like morphology that correlated with motility and invasiveness (Bittner et al., *Nature* 406:536-540, 2000). However, the clustering pattern could not be correlated with clinical or histological findings.

This example identifies three genes, IL-1 RI, endothelin-2, and ephrin-A5, as being differentially regulated in early melanoma (stage I, pT1) using a non-invasive skin sampling method. Although endothelin-1 and endothelin-3 have been previously linked to melanoma progression, an association between elevated levels of ephrin-2 and early melanoma has not been reported.

Although IL-1 RI has been reported to be linked to melanoma progression, these reports were based on cultured melanoma cells and were not skin cells from sample obtained using a non-invasive sampling method (Dekker et al., *Melanoma Res.* 7(3):223-230, 1997). Furthermore, Dekkar et al. 1997, is silent as to differential expression of IL-1 RI during a particular stage (i.e. early stage) of melanoma progression.

Ephrin-A5 has been reported to modulate cell adhesion and morphology (Robbins, *EMBO J.* 19(20):5396-5405, 2000). The ephrins are ligands for the Eph receptors, which are the largest known subfamily of receptor tyrosine kinases. ephrins are cell surface-associated proteins important for development, particularly in cell-cell interactions that promote processes such as nervous system patterning, angiogenesis, and oncogenesis.

Up-regulation of ephrin-A1 has been previously observed in melanoma biopsies, in increasing amounts in more advanced melanomas (Easty et al., *Int. J. Cancer* 84:494, 1999). Since the pro-inflammatory cytokines TNF-α and IL-1β both induce ephrin-A1 expression in melanoma cells, it was postulated that ephrin-A1 expression may be related to host inflammatory responses to advanced lesions. ephrin-A1 was also suspected to so promote vascularization of the tumor, thus contributing to further growth and metastasis (Easty et al., *Int. J. Cancer* 84:494, 1999). It is likely that ephrin-A5 contributes to melanoma progression through a similar mechanism.

The development of a molecular diagnostic screening test for early melanoma comprising the markers IL-1 RI, endothelin-2, and ephrin-A5, in combination with a non-invasive skin surface sampling method is described here. While the samples described here were obtained from frozen tissue, gene expression profiles are expected to be identical in freshly isolated human skin cell samples on the adhesive tape because the tissues used were snap frozen in Nitrogen immediately after excision and kept at −80° C. until the study was performed. Skin samples isolated on tape appear to be stable toward RNA degradation due to the relatively desiccated nature of stratum corneum cells. The markers identified here have utility in both diagnostic and prognostic applications and serve as aids for initial therapeutic decisions possibly saving many lives and reducing the cost of this safety by avoiding unnecessary excisions and biopsies.

TABLE 6

Actin AX/α/β/acidic
Adenosin Deaminase
B2m
BAGE
BAX
bcl-2
BFGF
brn-2/N-Oct3
c-jun, c-fos, jun-B
c-k-ras
c-kit
c-met
c-myc
c-ski
c-src-1
Calcyclin
Calmodulin
Cathepsin B, D
Cyclin A, B, D
CDK4
E-Cadherin
ECK
Endothelin-1 Rezeptor
EWS-ATF-1
FGF-Rezeptor-1
Sialyltransferase Familie
GM-CSF
gro/MGSA
H/Ki/K/N ras
H-2Db/H-2Kb
(MHC Klasse I)
HER2/neu
(Rezeptortyrosinkinase)
HOX Gene
(Homeoboxgene)
FGF Familie hst
ICAM1
IGF-1

TABLE 6-continued

IL1, 2, 6, 8, 10
IL4-Rezeptor
Integrine z.B. αVβ3
Interferon System
MHC Klasse II
Kollagenase (Gelatinase A/B,
Metalloproteinasen)
rap1-Krev1
Laminine
Lerk Familie
(Liganden der eph-verwandten
Rezeptortyrosinkinasen)
LRP
M-CSF
MAGE1/2
MCAF
MCP-1
mda-6 (p21), mda-7
MDR-1
Me14-D12
ME20
ME491
Mel-18
Melan-A
Methallothionein
MIA
Mitochondriale Gene
MnSOD
MRP
MSH-R
p15 (MTS2)
MUC18/MCAM
MYB
MZ2-E, F
n-myc
NF-1
Nma
Nmb
NME (nm23-1/2)
NSE
Ornithindecaboxylase
p-Glycoproteine
p16INK4 (CDKN2/MTS1)
p97
PAls
PCNA
PDGF
PKC isoformen
pp125FAK
PRB
Ribosomale Gene
S100
TAL1
TCL5
Tenascin
TGF α
TGF β 1, 2, 3
TGF β II Rezeptor
Thrombospondin
Thymosin β 10
TIMP-1
TNF α
TPA
Transglutaminase-TT
Tropomyosin 3
uPA-Rezeptoren
VEGF-R
Vinculin
Vitronectin-Rezeptor
VLA-1, 2, 4, 5
WT1

What is claimed is:

1. A non-invasive method for detecting early stage melanoma in a skin sample of a human subject, the method comprising:
   (a) obtaining a skin sample by applying at least one application of an adhesive to the skin of a human subject and removing the adhesive from the skin to remove a skin sample comprising RNA; and
   (b) detecting the level of lnterleukin-1 RI (IL-1 RI) RNA in the skin sample, wherein a decrease in the IL-1 RI RNA level, as compared to the RNA level in a control sample, is indicative of early stage melanoma, thereby detecting early stage melanoma in the skin sample.

2. The method of claim 1, further comprising detecting the RNA levels of endothelin-2 and ephrin-A5, and wherein a wherein a decrease in the level of IL-1 RI RNA, and an increase in the level of endothelin-2 or ephrin-A5 RNA levels, as compared to the RNA levels in a control sample, is indicative of early stage melanoma.

3. The method of claim 1, further comprising detecting RNA levels of one or more of markers selected from IGF Binding Protein 7, HLA-A0202 heavy chain, Activin A (βA subunit), TNF RII, SPC4, and CNTF Rα, wherein an increase in the RNA levels of the one or more markers, as compared to the RNA levels in a control sample, is indicative of melanoma.

4. The method of claim 1, further comprising detecting RNA levels of the markers IGF Binding Protein 7, HLA-A0202 heavy chain, Activin A (βA subunit), TNF RII, SPC4, and CNTF Rα wherein an increase in the RNA levels of these markers, as compared to the RNA levels in a control sample, is indicative of melanoma.

5. The method of claim 1, wherein the sample is obtained in a manner such that residual skin nucleic acid after removing the adhesive is not affected.

6. The method of claim 1, wherein the skin sample is isolated by applying the adhesive to the skin between one and two times to obtain the skin sample.

7. The method of claim 1, wherein the adhesive comprises an adhesive tape and the skin sample is isolated from a lesion suspected to be melanoma.

8. The method of claim 3, further comprising analyzing expression of one or more of the markers.

9. The method of claim 3, wherein the RNA comprises mRNA, and expression is analyzed by analyzing mRNA levels of one or more of the markers.

10. The method of claim 8, wherein expression of the skin markers is analyzed by detecting polynucleotides encoding the markers.

11. The method of claim 3, wherein the RNA levels of the markers are analyzed by applying the RNA to a microarray.

12. The method of claim 4, wherein RNA levels of IL-1 RI IGF Binding Protein 7, HLA-A0202 heavy chain, Activin A (βA subunit), TNF RII, SPC4, and CNTF Rα are detected in the skin sample, wherein a decrease in the level of IL-1 RI RNA is indicative of early stage melanoma, and an increase in the RNA levels of IGF Binding Protein 7, HLA-A0202 heavy chain, Activin A (βA subunit), TNF RII, SPC4, and CNTF Rα, as compared to the RNA levels in a control sample, is indicative of late stage melanoma.

13. A non-invasive method for monitoring the presence of melanoma in a human subject, the method comprising:
   (a) obtaining a first skin sample at a first time point by applying at least one application of an adhesive to the skin of a human subject and removing the adhesive from the skin to remove a skin sample comprising RNA;
   (b) detecting RNA levels in the first skin sample of the marker lnterleukin-1 RI (IL-1 RI);
   (c) obtaining a second skin sample at a second time point by applying at least one application of an adhesive to the skin of said human subject and removing the adhesive from the skin to remove a skin sample comprising RNA;
   (d) detecting RNA levels in the second skin sample of the marker IL-1 RI; and
   (e) comparing the RNA level of IL-1 RI at the first time point to the RNA level of IL-1 RI at the second time point to thereby monitor the presence of melanoma in the human subject, wherein a decrease in the level of IL-1 RI RNA, as compared to the RNA level in a control sample, is indicative of early stage melanoma.

14. The method of claim 13, wherein the skin sample is obtained in a manner such that residual skin nucleic acid after removing the adhesive is not affected, thereby obtaining a skin sample for use in isolating or detecting RNA in a skin sample.

15. The method of claim 12, further comprising detecting the RNA levels of endothelin-2 and ephrin-A5, and wherein a decrease in the level of IL-1 RI RNA and an increase in the RNA levels of endothelin-2 and ephrin-A5, as compared to the RNA levels in a control sample, is indicative of early stage melanoma.

16. The method of claim 12, further comprising detecting the RNA levels of IGF Binding Protein 7, HLA-A0202 heavy chain, Activin A (βA subunit), TNF RII, SPC4, and CNTF Rα, and wherein an increase in the RNA levels of IGF Binding Protein 7, HLA-A0202 heavy chain, Activin A (βA subunit), TNF RII, SPC4, and CNTF Rα, as compared to the RNA levels in a control sample, is indicative of late stage melanoma.

17. A non-invasive method for staging melanoma in a skin sample of a human subject, the method comprising:

(a) obtaining a skin sample by applying an adhesive surface to the skin of a human subject and removing the adhesive surface from the skin such that a skin sample comprising RNA in an amount sufficient for subsequent detection adheres to the adhesive surface after its removal; and (b) detecting the level of Interleukin-1 RI (IL-1 RI) RNA in the skin sample, wherein a decrease in the level of IL-1 RI RNA, as compared to the RNA level in a control sample, is indicative of early stage melanoma.

18. The method of claim 17, wherein the sample is obtained in a manner such that residual skin nucleic acid after removing the adhesive is not affected, thereby obtaining a skin sample for use in isolating or detecting RNA in a skin sample.

* * * * *